(12) United States Patent
Ito et al.

(10) Patent No.: US 9,228,725 B2
(45) Date of Patent: Jan. 5, 2016

(54) LIGHT SOURCE UNIT, OPTICAL CONVERSION UNIT, LIGHT SOURCE APPARATUS AND LIGHT SOURCE SYSTEM FOR AN ENDOSCOPE

(71) Applicant: OLYMPUS CORPORATION, Tokyo (JP)

(72) Inventors: Takeshi Ito, Hino (JP); Eiji Yamamoto, Musashimurayama (JP); Masahiro Nishio, Hachioji (JP); Iwao Komazaki, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/038,251

(22) Filed: Sep. 26, 2013

(65) Prior Publication Data
US 2014/0022810 A1  Jan. 23, 2014

Related U.S. Application Data

(63) Continuation of application No. PCT/JP2012/058333, filed on Mar. 29, 2012.

(30) Foreign Application Priority Data

Mar. 30, 2011  (JP) ................................ 2011-075282
Mar. 30, 2011  (JP) ................................ 2011-076078

(51) Int. Cl.
*F21V 17/00* (2006.01)
*A61B 1/07* (2006.01)
(Continued)

(52) U.S. Cl.
CPC ........... *F21V 17/002* (2013.01); *A61B 1/00126* (2013.01); *A61B 1/0638* (2013.01); *A61B 1/0653* (2013.01); *A61B 1/07* (2013.01); *F21V 9/10* (2013.01); *F21V 29/20* (2013.01); *G01N 21/8806* (2013.01); *G02B 6/0006* (2013.01);
(Continued)

(58) Field of Classification Search
CPC .......... F21V 17/002; F21V 29/20; F21V 9/10
See application file for complete search history.

(56) References Cited

U.S. PATENT DOCUMENTS 6,081,612 A * 6/2000 Gutkowicz-Krusin et al. ............................ 382/128
7,758,224 B2 * 7/2010 Hama et al. ................... 362/555
(Continued)

FOREIGN PATENT DOCUMENTS

CN  101027520 A  8/2007
EP  1 672 754 A2  6/2006
(Continued)

OTHER PUBLICATIONS

International Search Report dated Jul. 3, 2012 issued in PCT/JP2012/058333.
(Continued)

*Primary Examiner* — Thomas A Hollweg
(74) *Attorney, Agent, or Firm* — Scully, Scott, Murphy & Presser, P.C.

(57) ABSTRACT

A light source unit includes a primary light source configured to emit primary light, and a connection portion provided on an optical path of the primary light and to and from which an optical conversion unit is attachable and removable, the optical conversion unit including an optical conversion element configured to convert optical properties of the primary light to generate secondary light.

33 Claims, 13 Drawing Sheets

(51) Int. Cl.
*F21V 8/00* (2006.01)
*A61B 1/06* (2006.01)
*F21V 9/10* (2006.01)
*F21V 29/00* (2015.01)
*G01N 21/88* (2006.01)
*A61B 1/00* (2006.01)
*H01S 5/00* (2006.01)
*H01S 5/022* (2006.01)
*F21Y 101/02* (2006.01)
*H01S 5/40* (2006.01)
*F21V 29/85* (2015.01)

(52) U.S. Cl.
CPC ............ *F21V 29/85* (2015.01); *F21Y 2101/025* (2013.01); *H01S 5/0092* (2013.01); *H01S 5/02284* (2013.01); *H01S 5/4025* (2013.01)

(56) References Cited

U.S. PATENT DOCUMENTS

| | | | | |
|---|---|---|---|---|
| 8,488,930 | B2* | 7/2013 | Papac et al. | 385/116 |
| 2005/0010081 | A1* | 1/2005 | Doguchi et al. | 600/109 |
| 2005/0215861 | A1* | 9/2005 | Hakamata | 600/178 |
| 2006/0152926 | A1 | 7/2006 | Hama et al. | |
| 2006/0279950 | A1* | 12/2006 | Hama et al. | 362/257 |
| 2007/0010712 | A1 | 1/2007 | Negishi | |
| 2008/0089089 | A1* | 4/2008 | Hama et al. | 362/574 |
| 2009/0040598 | A1 | 2/2009 | Ito | |
| 2009/0059359 | A1 | 3/2009 | Nahm et al. | |
| 2009/0167149 | A1* | 7/2009 | Ito | 313/501 |
| 2009/0237011 | A1 | 9/2009 | Shah et al. | |
| 2009/0306478 | A1* | 12/2009 | Mizuyoshi | 600/178 |
| 2010/0113877 | A1 | 5/2010 | Suzuki | |
| 2010/0141747 | A1* | 6/2010 | Kubo et al. | 348/68 |
| 2010/0254153 | A1 | 10/2010 | Hama et al. | |
| 2010/0264829 | A1* | 10/2010 | Tojo et al. | 315/134 |
| 2011/0034770 | A1* | 2/2011 | Endo et al. | 600/118 |
| 2011/0077465 | A1* | 3/2011 | Mizuyoshi et al. | 600/180 |
| 2012/0116159 | A1* | 5/2012 | Mizuyoshi et al. | 600/109 |
| 2014/0022810 | A1 | 1/2014 | Ito et al. | |
| 2014/0146559 | A1 | 5/2014 | Ito et al. | |

FOREIGN PATENT DOCUMENTS

| | | |
|---|---|---|
| EP | 1 867 272 A1 | 12/2007 |
| EP | 2 301 414 A1 | 3/2011 |
| JP | 2001-215362 A | 8/2001 |
| JP | 2003-014984 A | 1/2003 |
| JP | 2006-61685 A | 3/2006 |
| JP | 2006-158716 A | 6/2006 |
| JP | 2006-173324 A | 6/2006 |
| JP | 2007-148288 A | 6/2007 |
| JP | 2008-29557 A | 2/2008 |
| JP | 2008-270229 A | 11/2008 |
| JP | 2009-39464 A | 2/2009 |
| JP | 2009-43668 A | 2/2009 |
| JP | 2009-106729 A | 5/2009 |
| JP | 2011-36361 A | 2/2011 |
| JP | 2011-41754 A | 3/2011 |
| WO | 2011/004801 A1 | 1/2011 |

OTHER PUBLICATIONS

Extended Supplementary European Search Report dated Apr. 1, 2015 from related European Application No. 12 81 1235.6.
Japanese Office Action dated Jan. 20, 2015 from related Japanese Patent Application No. 2011-075282, together with an English language translation.
Extended Supplementary Partial European Search Report dated Dec. 4, 2014 from related European Application No. 12 76 5608.0.
Chinese Office Action dated Jul. 23, 2015 from related Chinese Patent Application No. 201280015804.8 together with an English language translation.

* cited by examiner

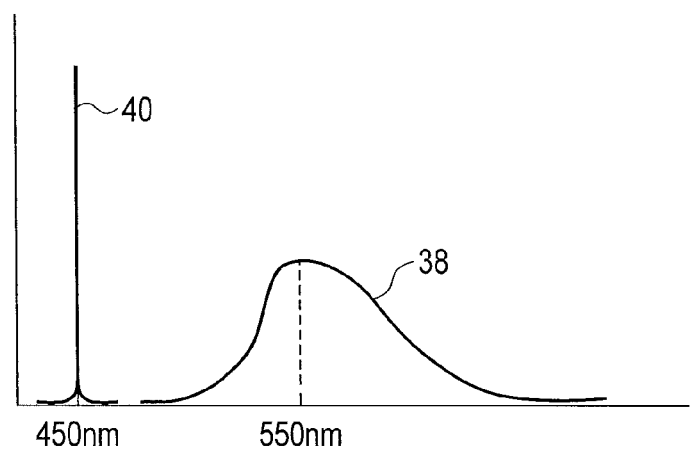
F I G. 4
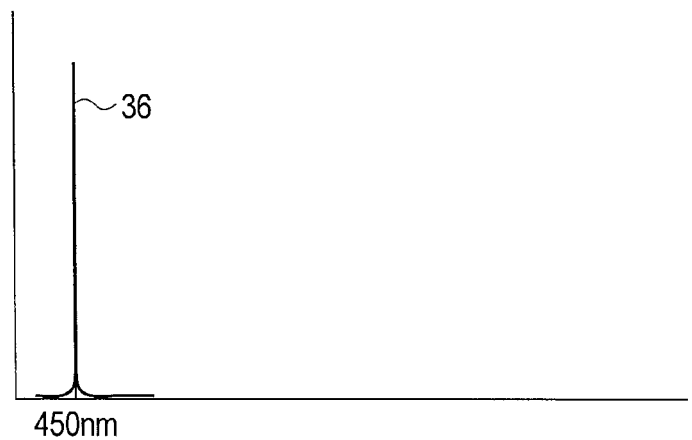
F I G. 5A
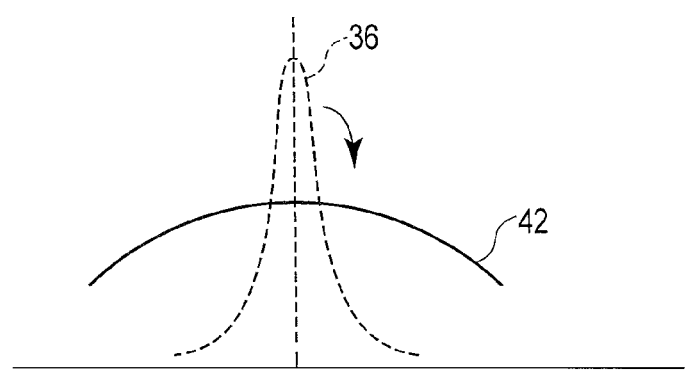
F I G. 5B

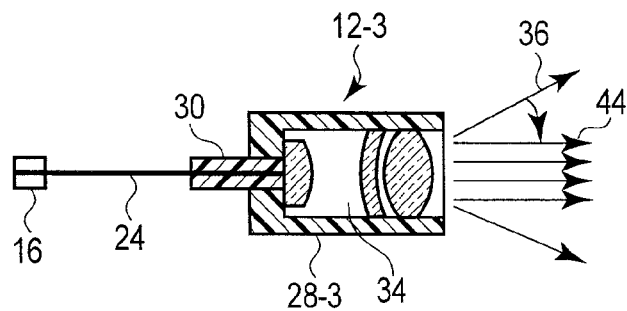
F I G. 6
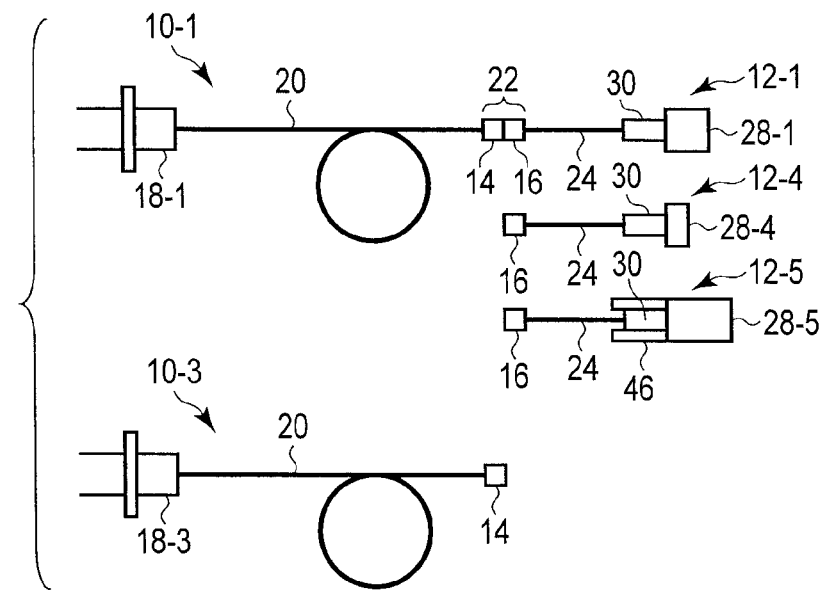
F I G. 7
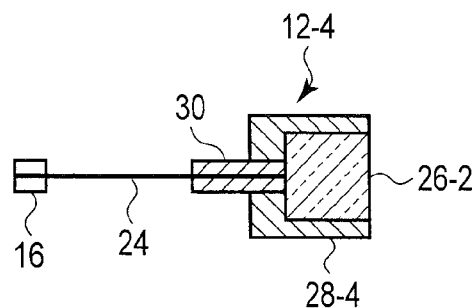
F I G. 8A

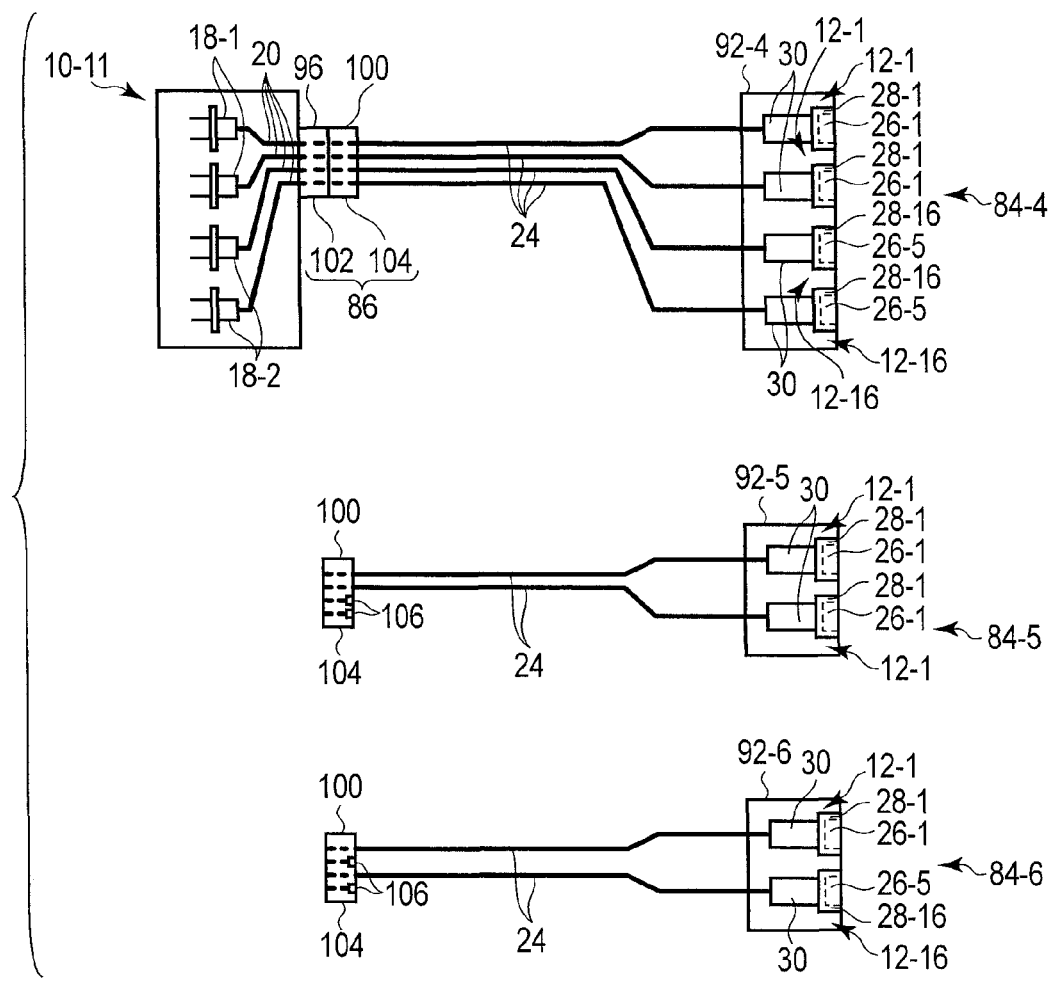
F I G. 19
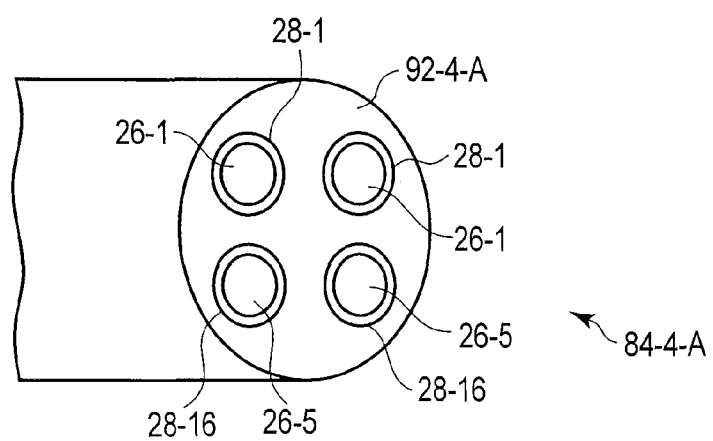
F I G. 20A

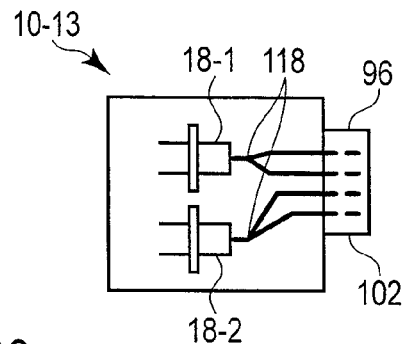
F I G. 23
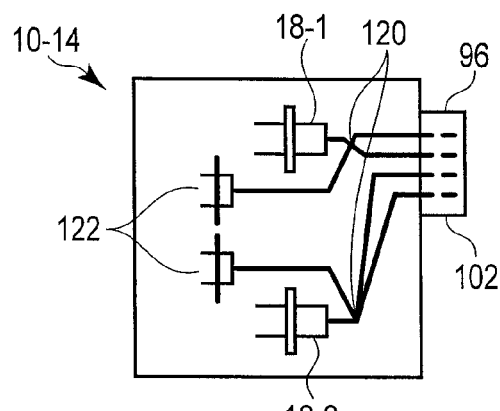
F I G. 24
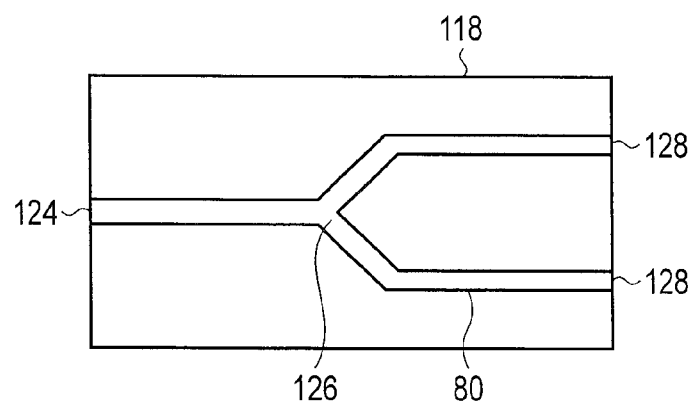
F I G. 25

LIGHT SOURCE UNIT, OPTICAL CONVERSION UNIT, LIGHT SOURCE APPARATUS AND LIGHT SOURCE SYSTEM FOR AN ENDOSCOPE

CROSS-REFERENCE TO RELATED APPLICATIONS

This is a Continuation application of PCT Application No. PCT/JP2012/058333, filed Mar. 29, 2012, which was published under PCT Article 21(2) in Japanese.

This application is based upon and claims the benefit of priority from prior Japanese Patent Applications No. 2011-075282 and NO. 2011-076078, both filed Mar. 30, 2011, the entire contents of which are incorporated herein by reference.

BACKGROUND OF THE INVENTION

1. Field of the Invention

The present invention relates to a light source unit, an optical conversion unit, a light source apparatus, and a light source system.

2. Description of the Related Art

U.S. Patent Application No. 2006/0152926 proposes a light emitting apparatus with a combination of a first unit with a second unit. In this case, the first unit uses a blue laser light source and a light guide to guides laser light emitted by the blue laser light source and also uses a wavelength conversion member provided at a distal end of the light guide to convert the wavelength of the laser light. The second unit uses a laser light source for a wavelength shorter than the wavelength of blue light, a light guide, and a wavelength conversion member. U.S. Patent Application No. 2006/0152926 discloses that the combination of the first unit with the second unit improves a color rendering index compared to the first unit alone.

In recent years, for observation light source apparatuses such as endoscopes, much effort have been made to improve the visibility of an observation target by appropriately selecting a brightness level, a peak wavelength, a luminescent color, that is, a spectral shape, a radiation angle, and the like according to the purpose of the observation.

In connection with such effort, to obtain light that meets the purpose, the light source apparatus in U.S. Patent Application No. 2006/0152926 needs preparation of units each using a laser light source, a light guide, and a wavelength conversion member and the number of which is equal to the number of types of light needed for the purpose. However, preparing a large number of units is difficult in a practical sense in terms of costs, a storage site, and the like.

BRIEF SUMMARY OF THE INVENTION

With the foregoing in view, it is an object of the present invention to enable various types of light to be radiated according to the purpose.

According to a first aspect of the invention, there is provided a light source unit comprising: a primary light source configured to emit primary light; and a connection portion provided on an optical path of the primary light and to and from which an optical conversion unit is attachable and removable, the optical conversion unit including an optical conversion element configured to convert optical properties of the primary light to generate secondary light.

According to a second aspect of the invention, there is provided a light source system comprising: the light source unit according to the first aspect of the invention; and an optical conversion unit group comprising a plurality of optical conversion units, and wherein the optical conversion units belonging to the optical conversion unit group are connectible to the light source unit by the connection portion.

According to a third aspect of the invention, there is provided an optical conversion unit comprising: an optical conversion element configured to convert optical properties of primary light to generate secondary light; and a connection portion provided on an optical path of the primary light and which is attachable to and removable from a light source unit with a primary light source configured to emit the primary light.

According to a fourth aspect of the invention, there is provided a light source apparatus comprising: a light source unit with a primary light source configured to emit primary light; a plurality of optical conversion units each having an optical conversion element configured to convert optical properties of the primary light to generate secondary light; a plurality of light guides configured to optically connect the primary light source to the plurality of optical conversion units by respective light guides; and a connection portion provided on each of the light guides, the primary light source and a corresponding one of the plurality of optical conversion units being attachable to and removable from the connection portion.

According to a fifth aspect of the invention, there is provided a light source system comprising a light source apparatus comprising: a light source unit with a primary light source configured to emit primary light; a plurality of optical conversion units each having an optical conversion element configured to convert optical properties of the primary light to generate secondary light; a plurality of light guides configured to optically connect the primary light source to the plurality of optical conversion units by respective light guides; and a connection portion provided on each of the light guides, the primary light source and a corresponding one of the plurality of optical conversion units being attachable to and removable from the connection portion, the plurality of optical conversion units being attached to a common optical conversion unit holding member to form an integrated optical conversion unit, first connection portions being integrated together to form a first integrated connection portion when the first connection portions included in the connection portion are attached to a light source unit side and second connection portions included in the connection portion are attached to an optical conversion unit side, the second connection portions being attached to one connection portion holding member to form a second integrated connection portion, the first integrated connection portion and the second integrated connection portion forming the removable integrated connection portion, wherein the integrated optical conversion unit forms an integrated optical conversion unit group together with a plurality of integrated optical conversion units different from the integrated optical conversion unit, and the integrated optical conversion units which are members of the integrated optical conversion unit group are all attachable to and removable from the light source unit at the integrated connection portion.

According to a sixth aspect of the invention, there is provided a light source system using a light source apparatus comprising: a light source unit with a primary light source configured to emit primary light; a plurality of optical conversion units each having an optical conversion element configured to convert optical properties of the primary light to generate secondary light; a plurality of light guides configured to optically connect the primary light source to the plurality of optical conversion units by respective light guides; and a connection portion provided on each of the light guides, the primary light source and a corresponding one of the plurality of optical conversion units being attachable to and removable from the connection portion, the plurality of optical conversion units being attached to a common optical conversion unit holding member to form an integrated optical conversion unit, first connection portions being integrated together to form a first integrated connection portion when the first connection portions included in the connection portion are attached to a light source unit side and second connection portions included in the connection portion are attached to an optical conversion unit side, the second connection portions being attached to one connection portion holding member to form a second integrated connection portion, the first integrated connection portion and the second integrated connection portion forming the removable integrated connection portion, wherein the light source unit forms a light source unit group together with a plurality of light source unit different from the light source unit, and members of the light source unit group are all attachable to and removable from members of the integrated optical conversion unit group at the integrated connection portion.

According to the present invention, because various light source units can be connected to various optical conversion units or by replacing the integrated optical conversion unit according to the purpose because the integrated optical conversion unit can be replaced for one light source unit. Therefore, any of various types of light meeting the purpose can be radiated by using a combination of the light source unit with the optical conversion unit which allows target light to be radiated.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a diagram illustrating a spectrum of light emitted when the first light source unit and the first optical conversion unit are combined together;

FIG. 5A is a diagram illustrating optical conversion characteristics of the second optical conversion unit, wherein the axis of ordinate represents light intensity and the axis of abscissas represents wavelength;

FIG. 5B is a diagram illustrating optical conversion characteristics of the second optical conversion unit, wherein the axis of ordinate represents light intensity and the axis of abscissas represents wavelength;

FIG. 6 is a diagram illustrating optical conversion characteristics of the third optical conversion unit;

FIG. 7 is diagram showing a configuration of a light source system according to a second embodiment of the present invention;

FIG. 8A is a cross-sectional view showing a configuration of a fourth optical conversion unit;

FIG. 19 is diagram showing a configuration of a light source system according to a seventh embodiment of the present invention;

FIG. 20A is a diagram showing a configuration of a fourth integrated optical conversion unit;

FIG. 23 is a diagram showing a thirteenth light source unit;

FIG. 24 is a diagram showing a fourteenth light source unit; and

FIG. 25 is a diagram illustrating an optical coupler according to a modification of the sixth and seventh embodiments.

DETAILED DESCRIPTION OF THE INVENTION

Embodiments of the present invention will be described below with reference to the drawings.

[First Embodiment]

First, a configuration of a light source system according to a first embodiment of the present invention will be described.

Figure 1:
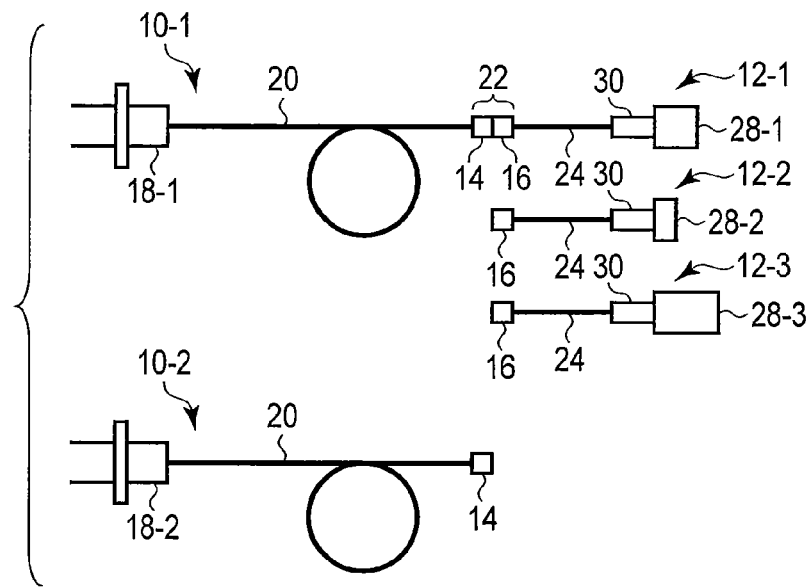
FIG. 1 is diagram showing a configuration of a light source system according to a first embodiment of the present invention.

As shown in FIG. 1, the light source system according to the present embodiment includes a light source unit group including a plurality of light source units 10-1 and 10-2 and an optical conversion unit group including a plurality of optical conversion units 12-1, 12-2, and 12-3. A light source apparatus can be configured by combining one light source unit 10-1 or 10-2 with one optical conversion unit 12-1, 12-2, or 12-3.

According to the present embodiment, each of the light source units 10-1 and 10-2 includes a connector 14 with a structure common to all of the light source units. Furthermore, all of the optical conversion units 12-1, 12-2, and 12-3 include a connector 16 that can be attached to and removed from the connector 14. Thus, all the members of the light source unit group can be connected to all the members of the optical conversion unit group in all combinations.

The light source system according to the present embodiment can deliver different types of illumination light simply by replacing the optical conversion unit 12-1, 12-2, or 12-3 for the light source unit 10-1 or 10-2.

As shown in FIG. 1, each of the light source units 10-1 and 10-2 includes a semiconductor laser 18-1 or 18-2, respectively, an optical fiber 20, and a connector 14. In this case, the semiconductor lasers 18-1 and 18-2 are primary light sources that emit primary light. The optical fiber 20 functions as a first light guide. The connector 14 is one of two connectors forming a connection portion 22 which is provided on an optical path for primary light traveling through the optical fiber 20 and to and from which any of the optical conversion units 12-1, 12-2, and 12-3 can be attached and removed.

The semiconductor laser 18-1 mounted on the first light source unit 10-1 is, for example, a blue semiconductor laser that emits blue light with a wavelength of about 450 nm. The semiconductor laser 18-1 and the optical fiber 20 are optically connected together by a lens (not shown in the drawings) or the like and configured such that blue laser light that is primary light emitted by the semiconductor laser 18-1 efficiently enters a core of the optical fiber 20. The blue laser light having entered the optical fiber 20 is guided via the connection portion 22 to the optical conversion unit 12-1, 12-2, or 12-3 connected to the connection portion 22.

Furthermore, in the second light source unit 10-2, the semiconductor laser 18-2 emits laser light with a wavelength different from the wavelength of laser light emitted by the semiconductor laser 18-1. The semiconductor laser 18-2 mounted on the light source unit 10-2 is, for example, a blue-violet semiconductor laser that emits blue-violet light with a wavelength of about 405 nm.

Figure 2A:
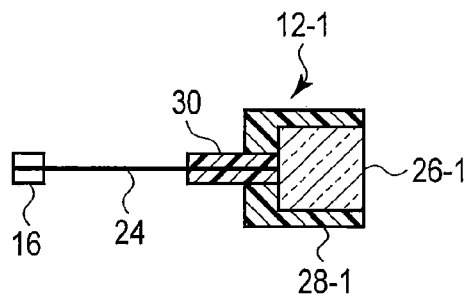
FIG. 2A is a cross-sectional view showing a configuration of a first optical conversion unit.

As shown in FIG. 2A, the first optical conversion unit 12-1 includes a connector 16, an optical fiber 24, a phosphor 26-1, and a holding member 28-1. The connector 16 is one of the two connectors forming the connection portion 22 which is provided on the optical path for the primary light, and can be attached to and removed from the connector 14 of the light source unit 10-1 or 10-2. The optical fiber 24 is a second light guide configured to guide the primary light from the connector 16 to a wavelength conversion member serving as an optical conversion element. The wavelength conversion member is inserted into the cylinder of the holding member 28-1, which is shaped like a bottomed cylinder. In the first optical conversion unit 12-1 according to the present embodiment, the wavelength conversion member is, for example, the phosphor 26-1, which absorbs the primary light to convert the primary light so as to shift to longer the peak wavelength thereof and to broaden the spectral shape and radiation angle.

The phosphor 26-1 is formed by mixing powdery fluorescent substance with resin, glass, or the like, which has the property of allowing the primary light to pass through, and solidifying the mixture. The holding member 28-1 includes an opening formed in the bottom surface of the cylinder and in which a ferrule 30 and the optical fiber 24 disposed in the ferrule 30 are interposed. According to the present embodiment, the fluorescent substance in the phosphor 26-1 is formed of Ce-doped yttrium aluminum garnet (YAG) phosphor mixed into a transparent silicone resin. The phosphor 26-1 is a shaped like a cylinder with a thickness adjusted such that optical characteristics of secondary light emitted by the phosphor 26-1 are optimum for observation light.

Figure 2B:
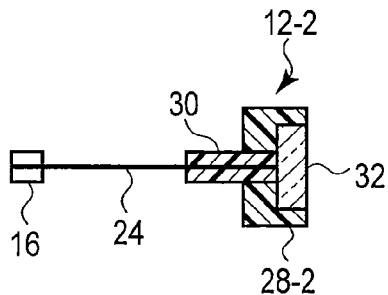
FIG. 2B is a cross-sectional view showing a configuration of a second optical conversion unit.

As shown in FIG. 2B, the second optical conversion unit 12-2 is basically configured similarly to the first optical conversion unit 12-1. The second optical conversion unit 12-2 is different from the first optical conversion unit 12-1 in a holding member 28-2 and an optical conversion element interposed in the holding member 28-2. The optical conversion unit 12-2 includes a radiation angle conversion element interposed therein as an optical conversion element. Specifically, the radiation angle conversion element is a diffusion member 32 that diffuses the primary light. The diffusion member 32 has a function to broaden the radiation angle of the primary light without converting the peak wavelength or spectral shape thereof. The diffusion member is formed by mixing, into a first member having the property of allowing the primary light to pass through, a second member with a refractive index different from the refractive index of the first member, and solidifying the mixture. For example, the diffusion member is formed by mixing a resin with a refractive index of 1.4 and a glass filler with a refractive index of 1.5. The diffusion member 32 has a thickness adjusted such that the optical characteristics of secondary light emitted by the diffusion member 32 are optimum for observation light.

Figure 2C:
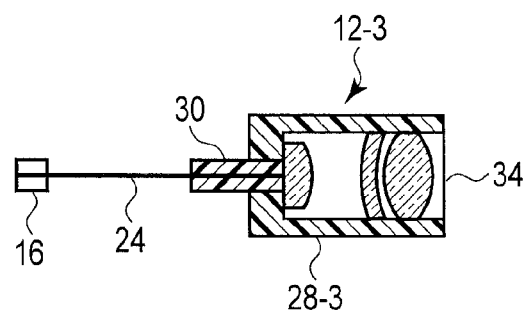
FIG. 2C is a cross-sectional view showing a configuration of a third optical conversion unit.

As shown in FIG. 2C, the third optical conversion unit 12-3 is basically configured similarly to the first optical conversion unit 12-1. The third optical conversion unit 12-3 is different from the first optical conversion unit 12-1 in a holding member 28-3 and an optical conversion element interposed in the holding member 28-3. The optical conversion element in the optical conversion unit 12-3 includes a collimate lens group 34 arranged in predetermined positional relationships to convert primary light into collimate light and to emit the collimate light as secondary light. The collimate lens group is set such that the emitted secondary light has an optimum beam diameter for observation light.

The material for the holding members 28-1, 28-2, and 28-3 is illustrated as resin in FIGS. 2A to 2C but is not particularly specified. Any material such as metal, resin, or ceramic may be used provided that the material enables the optical conversion element to be held.

Each of the optical fibers 20 and 24 is a common single optical fiber configured such that the core has a higher refractive index than a clad. The type of optical fiber is selected according to characteristics of a primary light source used in combination with the optical fiber. According to the present embodiment, the multimode semiconductor lasers 18-1 and 18-2 are used as a primary light source, and thus, the suitable type is a multimode fiber. Furthermore, the suitable optical fibers 20 and 24 have the same optical characteristics. This enables a reduction in loss on the connection portion 22. For example, a step index optical fiber may be used which has a core diameter of about 50 μm and a numerical aperture NA of about 0.22.

The connection portion 22 may be connectors that very efficiently connect the optical fibers 20 and 24 together.

Although not shown in the drawings, the connection portion has a function to align ferrules with each other via sleeves or the like for fixation. Common optical connectors may be used.

Now, the operation of the light source system according to the present embodiment will be described.

As described above, the light source system according to the present embodiment is configured such that the two light source units 10-1 and 10-2, the members of the light source unit group, can be connected, by the connection portion 22, to the three optical conversion units 12-1, 12-2, and 12-3, the members of the optical conversion unit group, in all combinations.

First, an operation will be described which is performed by a combination of the first light source unit 10-1 with any of the three optical conversion units 12-1, 12-2, and 12-3.

First, an operation will be described which is performed by a light source apparatus with a combination of the first light source unit 10-1 with the optical conversion unit 12-1.

The semiconductor laser 18-1 of the first light source unit 10-1 is connected to a power source and a control circuit that provide predetermined power to the first light source unit 10-1. The semiconductor laser 18-1 thus emits laser light with a wavelength of 450 nm. Blue laser light emitted by the semiconductor laser 18-1 is focused on a proximal end of the optical fiber 20 by a lens or the like (not shown in the drawings). The blue laser light enters the core of the optical fiber 20 and is guided through the optical fiber 20 and emitted from the connector 14 toward the connector 16 in the connection portion 22. The blue laser light delivered to the connector 16 enters the core of the optical fiber 24 and is guided through the optical fiber 24 and delivered to the phosphor 26-1, which is an optical conversion member interposed in the holding member 28-1 of the first optical conversion unit 12-1.

Figure 3A:
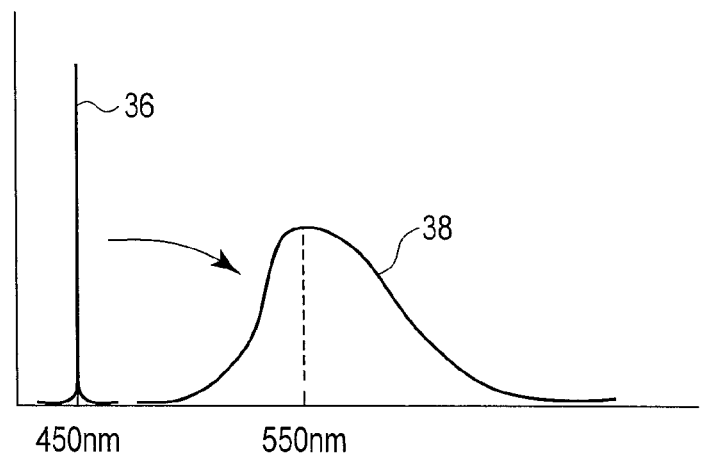
FIG. 3A is a diagram illustrating optical conversion characteristics of the first optical conversion unit, wherein the axis of ordinate represents light intensity and the axis of abscissas represents wavelength.
Figure 3B:
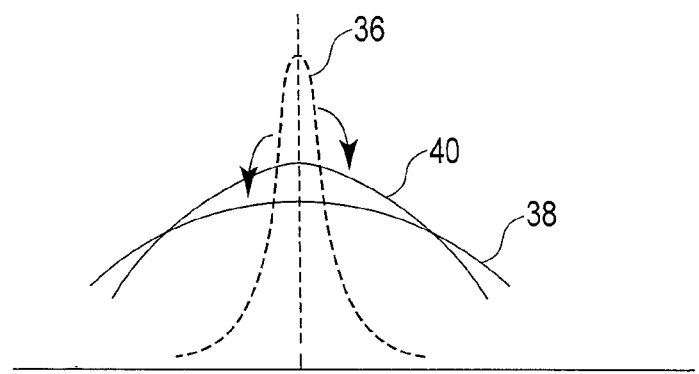
FIG. 3B is a diagram illustrating optical conversion characteristics of the first optical conversion unit, wherein the axis of ordinate represents light intensity and the axis of abscissas represents wavelength.

The blue laser light having entered the phosphor 26-1 is partly absorbed by the Ce-doped YAG, a fluorescent substance distributed in the phosphor 26-1. The blue laser light thus has the wavelength thereof converted and becomes yellow fluorescence, which is then radiated. That is, as shown in FIG. 3A, the phosphor 26-1 converts the peak wavelength from 450 to 550 nm, and for the spectral shape, converts a spectrum with a line width (full width at half maximum [FWHM]) of about 1 to 2 nm into a broad spectrum with a line width of 50 nm or more. Furthermore, another portion of the blue laser light having entered the phosphor 26-1 is scattered in the phosphor 26-1 and radiated to the exterior. Additionally, for the radiation angle, the Ce-doped YAG absorbs a portion of blue laser light 36 and emits yellow fluorescence 38 in various directions regardless of the direction in which the blue laser light 36 enters the phosphor 26-1, as shown in FIG. 3B. Thus, the yellow fluorescence 38 has a very wide radiation angle. Transmission light 40 contained in the blue laser light and scattered and radiated to the exterior instead of being absorbed by the phosphor 26-1 has a wider radiation angle than the blue laser light 36 as is not scattered. The transmission light 40 has a radiation angle substantially equal to the radiation angle of the yellow fluorescence 38.

That is, the first optical conversion unit 12-1 has a function to convert all of the peak wavelength, the spectral shape, and the radiation angle for a portion of the blue laser light and to convert only the radiation angle and avoid converting the peak wavelength and the spectral shape for the remaining portion of the blue laser light.

As a result, a light source apparatus with a combination of the first light source unit 10-1 with the first optical conversion unit 12-1 radiates illumination light serving as secondary light and having such a spectrum as shown in FIG. 4 and a radiation angle corresponding to the transmission light 40 and yellow fluorescence 38 of the blue laser shown in FIG. 3B. The illumination light is white light formed of blue light and yellow light that is a complementary color for the blue light. Thus, this combination enables provision of a light source apparatus that radiates white light.

Now, the operation of a light source apparatus with a combination of the first light source unit 10-1 with the second optical conversion unit 12-2 will be described. The basic operation of this light source apparatus is similar to the basic operation of the light source apparatus with the combination of the first light source unit 10-1 with the second optical conversion unit 12-1. Only differences between these light source apparatuses will be described.

Blue laser light emitted by the first light source unit 10-1 is delivered through the optical fiber 20, the connection portion 22, and the optical fiber 24 to the diffusion member 32 interposed inside the holding member 28-2 of the second optical conversion unit 12-2. The diffusion member 32 has a function to avoid converting the peak wavelength and spectral shape of the blue laser light and convert only the radiation angle of the blue laser light. FIG. 5A and FIG. 5B show the spectrum and radiation angle of illumination light radiated by the second optical conversion unit 12-2 configured as described above.

As shown in FIG. 5A, the spectrum has a wavelength of 450 nm and a spectral line width of 1 to 2 nm, which are the same as the wavelength and spectral line width of the laser light emitted by the semiconductor laser 18-1. On the other hand, as shown in FIG. 5B, the original laser light is blue laser light 42 having a much wider radiation angle than the laser light radiated from the optical fiber 24 (36 in FIG. 5B).

As a result, the combination of the first light source unit 10-1 with the second optical conversion unit 12-2 provides illumination light having the same wavelength and spectrum as those of the laser light and a wider radiation angle than the laser light. The illumination light with a wide radiation angle is also characterized in that the laser light provides significantly reduced coherence, thus making speckles and the like unlikely to occur.

Now, the operation of a light source apparatus with a combination of the first light source unit 10-1 with the third optical conversion unit 12-3 will be described. The basic operation of this light source apparatus is similar to the basic operations in the above-described two examples of combinations. Here, only differences will be described.

Blue laser light emitted by the first light source unit 10-1 is delivered through the optical fiber 20, the connection portion 22, and the optical fiber 24 to the collimate lens group 34 interposed in the holding member 28-3 of the third optical conversion unit 12-3. The blue laser light having entered the collimate lens group 34 is converted into collimate light beams 44 that are parallel light beams, and the collimate light beams 44 are delivered to the exterior. This is shown in FIG. 6, which is an image drawing. Without the collimate lens group, the blue laser light 36 would be radiated so as to have a divergence angle (36 in FIG. 6). In contrast, the collimate light beams 44 can be delivered to an illumination target with the beam diameter approximately unchanged. The third optical conversion unit 12-3 has a function to convert the blue laser light into parallel light beams, that is, has only a function to convert and narrow the radiation angle and an optical conversion function to avoid converting the peak wavelength and the spectral line width. As described above, the use of the third optical conversion unit 12-3 allows a remote illumination target to be illuminated with the beam diameter approximately unchanged. As a result, light beams with a relatively high power density can be delivered to the illumination target.

As described above, the combination of the first light source unit 10-1 with any of the three optical conversion units 12-1, 12-2, and 12-3 enables the single light source unit 10-1 to provide three different types of illumination light, that is, white light, laser diffused light, and collimate light.

Now, an operation will be described which is performed by a combination of the second light source unit 10-2, which emits blue-violet laser light with a wavelength of 405 nm, with any of the three optical conversion units 12-1, 12-2, and 12-3.

A basic operation in this case is similar to the basic operation in the case where the first light source unit 10-1 is used as described above. Thus, mainly differences will be described. The operation of the combination of the second light source unit 10-2 with either of the second and third optical conversion unit 12-2 and 12-3 is approximately equal to the operation of the combination of the first light source unit 10-1 with any of the optical conversion units and will thus not be described. Only the combination of the first light source unit 10-2 with the optical conversion unit 12-1 will be described.

That is, blue-violet laser light emitted by the second light source unit 10-2 is delivered through the optical fiber 20, the connection portion 22, and the optical fiber 24 to the phosphor 26-1 interposed in the holding member 28-1 of the first optical conversion unit 12-1. The Ce-doped YAG of the phosphor 26-1 absorbs much of the blue light with a wavelength of 450 nm to perform a wavelength conversion to convert the blue light into yellow fluorescence, but absorbs little of the blue-violet light with a wavelength of 405 nm, thus involving substantially none of such a wavelength conversion as shown in FIG. 3A. That is, the phosphor 26-1 serving as an optical conversion element absorbs two types of primary light at different absorption rates, and thus, absorbs much of the primary light with a wavelength of 450 nm to convert the primary light into white light but absorbs little of the primary light with a wavelength of 405 nm to emit the primary light without any change. However, the Ce-doped YAG, a fluorescent member arranged in the phosphor 26-1 in a distributed manner, has a refractive index of about 1.8, which is larger than the refractive index of common glass or resin, which is used for sealing; the common glass or resin or the like has a refractive index of about 1.4 to about 1.5. Thus, the phosphor 26-1 interposed in the first optical conversion unit 12-1 acts on the blue-violet laser light in a manner substantially equal to the manner in which the diffusion member 32 acts on the blue-violet laser light. That is, as shown in FIG. 5A and FIG. 5B, an optical conversion is carried out so as to broaden only the radiation angle, with the peak wavelength and the spectral shape substantially unconverted. In other words, for the second light source unit 10-2, the first optical conversion unit 12-1 provides an optical conversion function similar to the optical conversion function of the second optical conversion unit 12-2 with the diffusion member 32.

That is, when white light and diffusion light of blue-violet light are to be used for observation, the observation can be achieved simply by preparing the two light source unit 10-1 and 10-2 and combining each of the light source unit 10-1 and 10-2 with the first optical conversion unit 12-1.

As described above, various types of illumination light can be obtained by appropriately combining the members of the light source unit group with the members of the optical conversion unit group.

As described above, according to the first embodiment, the connection portion 22 is provided at a primary light output end of each of the light source units 10-1 and 10-2 and configured such that any of the various optical conversion units 12-1, 12-2, and 12-3 can be attached to and removed from the connection portion 22. In the light source system according to the first embodiment, the various light source units 10-1 and 10-2 and optical conversion units 12-1, 12-2, and 12-3 are prepared and connected together by the compatible connection portion 22, so that various combinations can be made. Thus, various types of illumination light can be provided by a reduced number of members.

Such a conventional configuration as disclosed in the U.S. Patent Application No. 2006/0152926 needs units each with a combination of a light source unit with an optical conversion unit the number of which is equal to the number of types of illumination light. In contrast, the first embodiment can provide a number of types of illumination light the number of which is equal to the number of light source units multiplied by the number of optical conversion units. A large number of types of illumination light can be very effectively produced using a small number of members.

Furthermore, if a space in which the optical conversion units are mounted is limited as is the case with an endoscope or the like, such a conventional configuration as disclosed in the U.S. Patent Application No. 2006/0152926 limits the number of types of illumination light that can be emitted. In contrast, the configuration according to the present embodiment provides various types of illumination light by preparing a number of light source units and a number of optical conversion units the numbers of which correspond to the needed types of illumination light (for example, the light source units 10-1 and 10-2 and the optical conversion units 12-1, 12-2, and 12-3) and appropriately replacing the light source units and the optical conversion units.

That is, a light source system can be provided which allows a light source apparatus capable of radiating various types of light to be arranged with high space efficiency by appropriately selecting a combination of either of the light source units 10-1 and 10-2 with any of the optical conversion units 12-1, 12-2, and 12-3.

The configuration shown in FIG. 1 of the first embodiment is only an example and only illustrates a simplified system with two types of light source units (light source units 10-1 and 10-2) and three types of optical conversion units (optical conversion units 12-1, 12-2, and 12-3) for simplification. For practical use, more light source units and more optical conversion units may be appropriately prepared according to the needed functions of the illumination light. The primary light source mounted on the light source unit is not limited to the semiconductor laser but may be any of various light sources such as various laser light sources, LEDs, and lamps. More desirably, the light source can be efficiently connected to an optical fiber.

The optical conversion element mounted in the optical conversion unit is also not limited to the above-described phosphor, diffusion member, and collimate lens system but may be any of various optical conversion elements. Examples of the usable optical conversion element include not only various powdery phosphors, ceramic phosphors, and single crystal phosphors, but also a quantum dot, a semiconductor light emitting element, and an organic light emitting element. Furthermore, the diffusion member may be of a type including a transparent member the surface of which is processed to include recesses and protrusions. Moreover, when a directional optical conversion element such as a diffraction grating, a polarizing element, or a photonic crystal is used, the radiation angle or intensity distribution of emitted secondary light can be made directional. In addition, the use of various wavelength filters enables only the light in the desired wavelength range to be extracted or cut.

Moreover, in the present embodiment, only the example in which the single optical conversion element is used has been described. However, the present embodiment is not limited to the embodiment. A plurality of optical conversion elements can be mounted in one holding member. For example, when a filter that cuts a portion of the wavelength of fluorescence is disposed on an output surface of the phosphor, exclusively the fluorescence in the desired wavelength region can be extracted. Furthermore, mounting a filter that cuts the primary light enables only the fluorescence to be extracted.

[Second Embodiment]

Now, a second embodiment of the present invention will be described.

The basic configuration of the second embodiment is the same as the basic configuration of the first embodiment. Thus, only differences from the first embodiment will be described.

A light source system according to the present embodiment is configured as shown in FIG. 7 and basically configured similarly to the light source system according to the first embodiment. The second embodiment is different from the first embodiment in the organization of the members of a light source unit group and the organization of the members of an optical conversion unit group.

That is, the light source unit group according to the present embodiment includes two light source unit 10-1 and 10-3 as members. The first light source unit 10-1 includes a semiconductor laser 18-1 that emits 450-nm blue laser light. Furthermore, the third light source unit 10-3 similarly includes a semiconductor laser 18-3 that emits 450-nm blue laser light. The two semiconductor lasers 18-1 and 18-3 are different from each other in the maximum intensity of light that can be output, that is, the maximum optical output. The semiconductor laser 18-1 is a blue semiconductor laser with a maximum optical output of 100 mW. On the other hand, the semiconductor laser 18-3 is a blue semiconductor laser with a maximum optical output of 1,000 mW.

The remaining part of the configuration is similar to the corresponding part of the configuration of the first embodiment.

The optical conversion unit group according to the present embodiment includes three optical conversion units 12-1, 12-4, and 12-5 as members. The first optical conversion unit 12-1 includes a holding member 28-1 with a phosphor 26-1 interposed therein as is the case with the first embodiment. Furthermore, the fourth optical conversion unit 12-4 includes a holding member 28-4 with a phosphor 26-2 interposed therein and which is different from the phosphor 26-1. The fifth optical conversion unit 12-5 uses the phosphor 26-1 and includes a holding member 28-5 with a thermal radiation member 46 connected thereto.

Of the three optical conversion units, the two optical conversion units 12-4 and 12-5 will be described, which are different from the corresponding optical conversion units in the first embodiment.

As shown in FIG. 8A, the fourth optical conversion unit 12-4 appears similar to the first optical conversion unit 12-1 shown in FIG. 2A. The phosphor 26-1 in the first optical conversion unit 12-1 includes Ce-doped YAG solidified in a silicone resin in a distributed manner. In contrast, a phosphor 26-2 in the fourth optical conversion unit 12-4 includes a powder of Ce-doped YAG which is a fluorescent substance and which is dispersed in glass in order to improve thermal resistance. The Ce-doped YAG, which is a fluorescent substance, offers sufficiently high thermal resistance, whereas the silicone resin may be yellowed or subjected to cracks or the like to exhibit degraded performance as an optical conversion element when held at higher than about 200° C. for a long time. In comparison, the phosphor 26-2 using glass does not substantially have its performance degraded even at high temperatures greater than or equal to 400° C.

The holding member 28-4 of the fourth optical conversion unit 12-4 is shaped similarly to the holding member 28-1 of the first optical conversion unit 12-1 but is formed of a highly heat-resistant material. As described above, any holding member 28-1 may be used provided that the holding member 28-1 can hold the phosphor 26-1. In contrast, the holding member 28-4 is a highly heat-resistant material, for example, metal or ceramic.

In the above-described configuration, the fourth optical conversion unit 12-4 can offer higher thermal resistance than the first optical conversion unit 12-1.

Figure 8B:
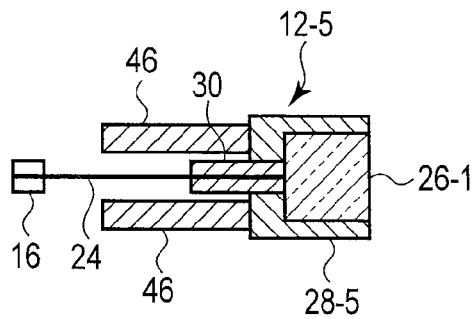
FIG. 8B is a cross-sectional view showing a configuration of a fifth optical conversion unit.

As shown in FIG. 8B, the fifth optical conversion unit 12-5 includes a phosphor 26-1 mounted therein as an optical conversion element positioned inside a holding member 28-5, the phosphor 26-1 being similar to the phosphor in the first optical conversion unit 12-1. The holding member 28-5 is formed of a highly thermally conductive member. The highly thermally conductive member is, for example, aluminum or copper. Furthermore, any highly thermally conductive member other than metal may be used. The appropriate thermal conductivity of the usable highly thermally conductive member is 0.1 W/m·K or higher. The appropriate thermal conductivity is desirably 1.0 W/m·K or higher.

A metal wire as a thermal radiation member 46 is connected to the holding member 28-5. The metal wire is formed of copper or the like, which has high thermal conductivity, and is thermally connected to the holding member 28-5. The thermal radiation member 46 may also be any highly thermally conductive member other than the metal wire, for example, a metallic rod or mesh or carbon fiber. The appropriate thermal conductivity of the usable thermal radiation member 46 is 0.1 W/m·K or higher. The appropriate thermal conductivity is desirably 1.0 W/m·K or higher.

Now, the operation of the light source system according to the second embodiment will be described. The operation of the light source system according to the second embodiment is basically the same as the operation of the light source system according to the first embodiment. Here, only differences from the first embodiment will be described.

For light source apparatuses with all possible combinations of the light source units 10-1 and 10-3 and the optical conversion units 12-1, 12-4, and 12-5, a series of operations of turning blue laser light radiated by the light source unit 10-1 or 10-3 into white illumination light are similar to corresponding operations according to the first embodiment.

First, the operation of a light source apparatus with a combination of the first light source unit 10-1 with the fourth optical conversion unit 12-4 will be described. The fourth optical conversion unit 12-4 uses a highly heat-resistant phosphor 26-2 and a highly heat-resistant holding member 28-4. Thus, the fourth optical conversion unit 12-4 can be used at high temperatures greater than or equal to 100° C., at which the first optical conversion unit 12-1 may suffer functional deterioration as a result of degradation of the member. For example, even when inserted into an engine for use immediately after the engine stops, the fourth optical conversion unit 12-4 does not substantially suffer functional deterioration as a result of degradation of the member.

Now, the operation of a light source apparatus with a combination of the first light source unit 10-1 with the fifth optical conversion unit 12-5 will be described. The fifth optical conversion unit 12-5 is configured to easily radiate heat resulting from optical conversion by the phosphor 26-1 to the exterior of the optical conversion unit 12-5 using the holding member 28-5 and the thermal radiation member 46. Thus, the fifth optical conversion unit 12-5 can be maintained at a lower surface temperature than the first optical conversion unit 12-1, including no thermal radiation member. For example, when the optical conversion unit may come into contact with a living organism during use, this light source apparatus may reduce the risk of thermal destruction of the living tissue. Even for an endoscope or the like, which is used for the human body, the light source unit apparatus can reduce the risk of a burn or the like.

Now, the operation of a light source apparatus with a combination of the third light source unit 10-3 with any of the optical conversion units 12-1, 12-4, and 12-5 will be described. The third light source unit 10-3 includes a blue semiconductor laser 18-3 with a maximum optical output of 1,000 mW, which is 10 times as much as the maximum optical output of the blue semiconductor laser 18-1 mounted on the first light source unit 10-1, which is 100 mW. Heat generated during a process in which a phosphor absorbs blue laser light to emit yellow fluorescence is generally proportional, in amount, to the intensity of incident light. Thus, heat generated by the phosphor 26-1 when the third light source unit 10-3 emits light at the maximum output is about 10 times as much as heat generated by the phosphor 26-1 when the first light source unit 10-1 emits light at the maximum output.

First, the operation of a light source apparatus with a combination of the third light source unit 10-3 with the first optical conversion unit 12-1 will be described. Since the third light source unit 10-3 has a higher maximum optical output than the first light source unit 10-1, the third light source unit 10-3 can increase brightness up to the limit of the first optical conversion unit 12-1. That is, the third light source unit 10-3 allows bright illumination light to be obtained until the local temperature of the first optical conversion unit 12-1 reaches the thermal resistance temperature limit of the silicone resin as a result of heat generation involved in optical conversion. However, when, for example, silicone with a thermal resistance temperature limit of 200° C. is used as the phosphor 26-1, if even a part of the silicone resin exceeds the thermal resistance temperature limit, the resin in the phosphor 26-1 may be yellowed or cracked. Thus, the brightness of the light source unit can no longer be increased.

In such a case, the use of the fourth optical conversion unit 12-4 with improved thermal resistance enables a further increase in brightness. The fourth optical conversion unit 12-4 is formed of a more thermally-resistant member than the first optical conversion unit 12-1. Thus, the combination of the fourth optical conversion unit 12-4 with the third light source unit 10-3 provides brighter illumination light than the combination of the first optical conversion unit 12-1 with the third light source unit 10-3. Compared to the phosphor 26-1, the phosphor 26-2, including Ce-doped YAG dispersed in glass, serves to significantly improve thermal resistance. For example, the phosphor 26-2 has a low possibility of being degraded even when 1,000-mW primary light enters the phosphor 26-2. Furthermore, at an elevated atmospheric temperature, the phosphor has a consistently increased local temperature and is likely to be degraded even by an intensity of primary light that does not affect the phosphor at room temperature. However, the combination of the fourth optical conversion unit 12-4 with the third light source unit 10-3 can be used even for observation in an environment at elevated temperatures.

Now, the operation of a light source apparatus with a combination of the third light source unit 10-3 with the fifth optical conversion unit 12-5 will be described. The fifth optical conversion unit 12-5 is configured to efficiently release heat generated by the phosphor 26-1 to the exterior. Thus, the fifth optical conversion unit 12-5 not only enables a reduction in the risk of affecting the living organism as described in connection with the combination of the first light source unit 10-1 with the first optical conversion unit 12-1, but also allows local heat generation by the phosphor 26-1 to be reduced by thermal radiation. As a result, even the use of the phosphor 26-1 with the same thermal resistance enables brighter light emission.

As described above, the light source system according to the second embodiment can mitigate degradation of the phosphor 26-1 or 26-2 and reduce an increase in the local temperature the phosphor 26-1 or 26-2 by using the optical conversion units 12-1, 12-4, and 12-5 with different thermal resistance properties and different thermal radiation properties.

That is, when the optical conversion units 12-4 and 12-5 are prepared which have improved thermal resistance and radiation compared to the optical conversion unit 12-1, brighter illumination light can be obtained, observation at elevated temperatures can be achieved, and the risk of affecting the living organism can be reduced. Furthermore, if the thermal resistance or radiation is unwanted, implementation of the corresponding function may be avoided to provide a simpler and less expensive optical conversion unit 12-1.

The above-described configuration is only an example, and for example, an optical conversion unit with a combination of the highly thermally resistant phosphor 26-2 with the thermal radiation member 46 can be produced. Thus, a light source apparatus allowing the use of elevated temperatures and excitation light with high intensity can be maintained at a low surface temperature.

Furthermore, the example in which the phosphors 26-1 and 26-2 provide white light has been illustrated. However, the present embodiment is not limited to the example. Even when a diffusion member 32 is used to convert the radiation angle, the diffusion member may be formed using a highly thermally resistant member as a base material or the thermal radiation member 46 may be provided. Thus, the diffusion member allows the use of elevated temperatures and high intensity light, and heat generation by the diffusion member in connection with optical diffusion can be reduced. This also applies to the use of an optical conversion element such as a filter which generates heat in connection with optical conversion.

[Third Embodiment]

Now, a third embodiment of the present invention will be described.

The basic configuration of the third embodiment is the same as the basic configuration of the first embodiment. Here, only differences from the first embodiment will be described.

The light source system according to the third embodiment is basically configured similarly to the light source system according to the first embodiment. The third embodiment is different from the first embodiment in the organization of the members of an optical conversion unit group, and a light source unit group according to the third embodiment is different from the light source unit group according to the first embodiment in that the light source unit group according to the third embodiment has only the first light source unit 10-1 as a member.

Third embodiment has the same optical conversion function as that of the first and second embodiments but is different from the first and second embodiments in the shape and size of a holding member provided at a distal end of an optical conversion unit.

Figure 9A:
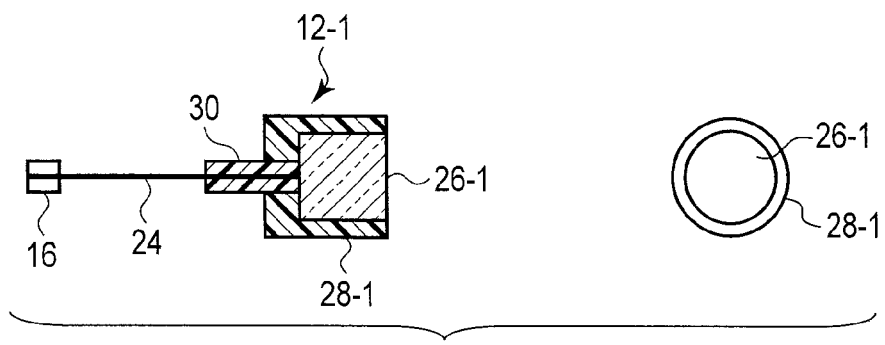
FIG. 9A is a diagram showing a configuration of a first optical conversion unit in a light source system according to a third embodiment of the present invention.
Figure 9B:
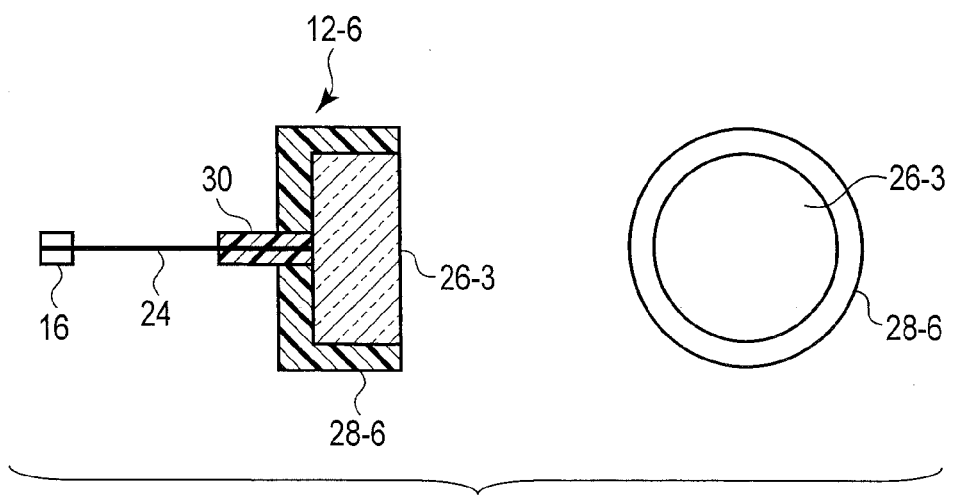
FIG. 9B is a cross-sectional view showing a configuration of a sixth optical conversion unit.
Figure 9C:
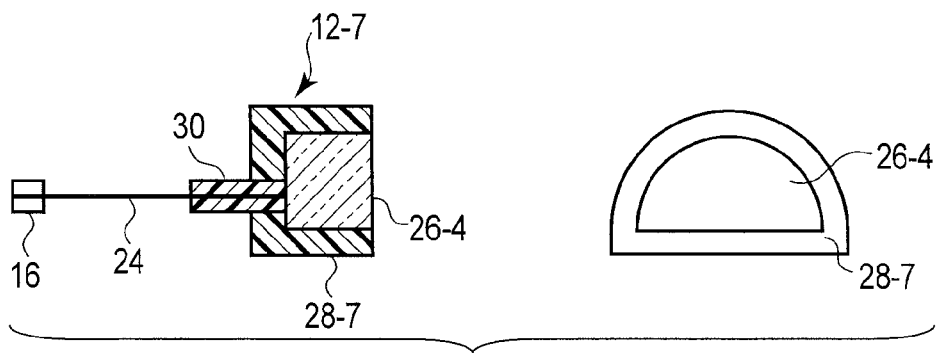
FIG. 9C is a cross-sectional view showing a configuration of a seventh optical conversion unit.

That is, the optical conversion unit group according to the third embodiment includes three optical conversion units 12-1, 12-6, and 12-7 as members as shown in FIG. 9A to FIG. 9C. In FIG. 9A to FIG. 9C, a figure shown on the left side is a cross-sectional view showing the central axis of an optical fiber 24, and a figure shown on the right is a front view of the optical conversion unit as seen from a secondary light output side, that is, from the right side of the figure shown on the left side. The basic structure of each of the optical conversion units 12-1, 12-6, and 12-7 is similar to that of the first optical conversion unit 12-1 illustrated in the first embodiment. However, the sixth and seventh optical conversion units 12-6 and 12-7 are different from the first optical conversion unit 12-1 only in the sizes and shapes of the holding member and the phosphor.

The first optical conversion unit 12-1 shown in FIG. 9A is the same as the first optical conversion unit 12-1 described in the first embodiment and shown in FIG. 2A. FIG. 9B is a diagram showing the sixth optical conversion unit 12-6 with the phosphor 26-1 and holding member 28-1 of the first optical conversion unit 12-1 increased in radial size (a phosphor 26-3 and a holding member 28-6, respectively). The phosphor 26-3 has the same thickness as that of the phosphor 26-1. FIG. 9C is a diagram showing the seventh optical conversion unit 12-7. A phosphor 26-4 is one of two pieces into which the phosphor 26-3 is cut, and a holding member 28-7 is shaped to be suitable for holding the phosphor 26-4.

Now, the operation of the light source system according to the third embodiment will be described. For all possible combinations of the members belonging to the light source unit group and the members belonging to the optical conversion unit group, a series of operations of turning blue laser light into white illumination light are similar to the operations of the combination of the first light source unit 10-1 with the optical conversion unit 12-1 according to the first embodiment.

Optical conversion units such as the first optical conversion unit 12-1 which have small distal end diameters emit light from small points and are thus similar to point light source. The sixth optical conversion unit 12-6, which is large in size, emits light more similarly to a surface light source than to a point light source. Furthermore, light distribution and the like vary depending on the shape.

As described above, the light source system according to the third embodiment allows selection of any of the optical conversion units 12-1, 12-6, and 12-7 which has the suitable size and shape for limitations on the place where the optical conversion units are mounted.

The third embodiment exerts the following effect in addition to the effects illustrated in the first embodiment. That is, a distal end unit can be selected so as to achieve the optimum space efficiency for an area where an illumination apparatus is mounted simply by appropriately selecting any of the optical conversion units 12-1, 12-6, and 12-7 for the one light source unit 10-1. For example, when the optical conversion unit is combined with an imaging device or the like or needs to be mounted in a small space such as in an endoscope, the suitable optical conversion unit can be selected so as to effectively utilize the space in the gap between the optical conversion unit and another member.

The shapes and sizes shown in FIG. 9A to FIG. 9C are only examples, and the shape and size may be modified in various ways. Optical conversion units can be produced which have different shapes including an ellipse and a square and selected taking mounting of an imaging device into account.

Furthermore, the optical conversion element is not limited to the phosphor but any of various optical conversion elements may be used such as an optical conversion element such as a diffusion member or a collimate lens group which converts only the radiation angle, a wavelength selection filter, and a combination thereof.

[Fourth Embodiment]

Now, a fourth embodiment of the present invention will be described.

The basic configuration of the fourth embodiment is the same as the basic configuration of the first embodiment. Here, only differences from the first embodiment will be described.

A light source system according to the fourth embodiment is different from the light source systems according to the first to third embodiments in the position of a connection portion to and from which a light source unit and an optical conversion unit are attached and removed.

Figure 10:
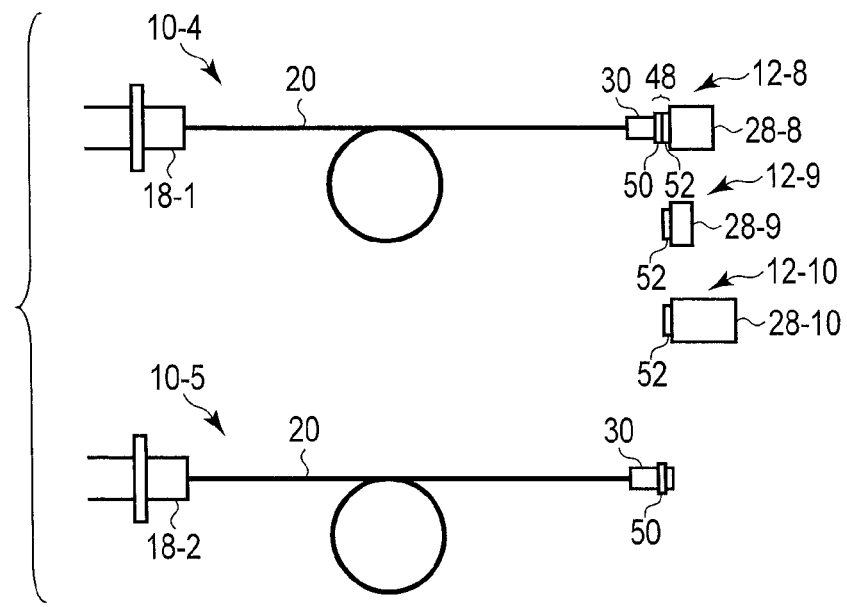
FIG. 10 is diagram showing a configuration of a light source system according to a fourth embodiment of the present invention.

That is, as shown in FIG. 10, the light source system according to the present embodiment is different from the light source system according to the first embodiment in that a connection portion 48 is provided between a ferrule 30 and a holding member rather than on an optical fiber 20 serving as a light guide. A fourth light source unit 10-4 and a fifth light source unit 10-5 and an eighth optical conversion unit 12-8, a ninth optical conversion unit 12-9, and a tenth optical conversion unit 12-10 are different from the first and second light source units 10-1 and 10-2 and the first, second, and third optical conversion units 12-1, 12-2, and 12-3 illustrated in the first embodiment only in the position and structure of the connection portion. The above-described units of the fourth embodiment have the same optical functions as those of the above-described units of the first embodiment corresponding to the units of the fourth embodiment in the above-described order.

Each of the fourth and fifth light source units 10-4 and 10-5 includes a semiconductor laser 18-1 or 18-2, respectively, the optical fiber 20, the ferrule 30, and a connector 50 of the connection portion 48 as shown in FIG. 10. Although the connection portion 48 is partly omitted from FIG. 10 for simplification, the connector 50 and a connector 52 have a fitting structure such as a joint which allows the connectors 50 and 52 to be fixed to each other.

The connection portion 48 has a positioning function to place the ferrule 30 in the optimum positional relationship with an optical conversion element in a holding member 28-8, 28-9, or 28-10.

Figure 11A:
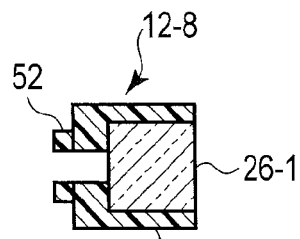
FIG. 11A is a cross-sectional view showing a configuration of an eight optical conversion unit.
Figure 11B:
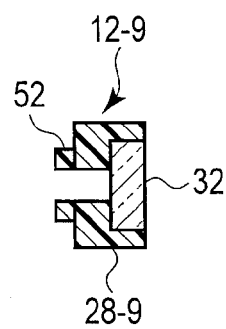
FIG. 11B is a cross-sectional view showing a configuration of a ninth optical conversion unit.
Figure 11C:
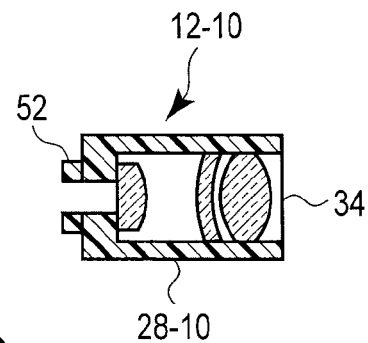
FIG. 11C is a cross-sectional view showing a configuration of a tenth optical conversion unit.

FIGS. 11A to 11C show cross-sectional views of the eighth, ninth, and tenth optical conversion units 12-8, 12-9, and 12-10, which are the members of the optical conversion unit group according to the present embodiment.

A connector 52 of the connection portion 48 is formed on each of optical conversion units 12-8, 12-9, and 12-10. Connector 52 is shaped like a ring and includes a through-hole formed therein into which the ferrule 30 is fitted.

When the ferrule 30 disposed at the distal end of the optical fiber from the fourth or fifth light source unit 10-4 or 10-5 is inserted through the through-hole in the connector 52 and through a through-hole in the holding member 28-8, 28-9, or 28-10, the connectors 50 and 52 are fitted and fixed together at a position where an end of the ferrule 30 substantially contacts a phosphor 26-1, a diffusion member 32, or a collimator lens group 34.

For all possible combinations of the members belonging to the light source unit group and the members belonging to the optical conversion unit group, the basic operation of the light source system according to the fourth embodiment described above is similar to the basic operation described in the first embodiment.

As described above, the light source system according to the fourth embodiment allows the structures of the optical conversion units 12-8, 12-9, and 12-10 to be simplified without substantially complicating the structure of the light source unit. Thus, the light source system according to the fourth embodiment is suitable for a reduction in size and costs.

Thus, the sizes and costs of the optical conversion units 12-8, 12-9, and 12-10 can be reduced, allowing many optical conversion units to be easily held and stored. Furthermore, exclusively the distal end of a light source apparatus may be replaced. Hence, even when, for example, the light source apparatus is incorporated into an endoscope or the like, the fourth embodiment enables a replacement operation to be performed more easily than the first to third embodiments.

Figure 12:
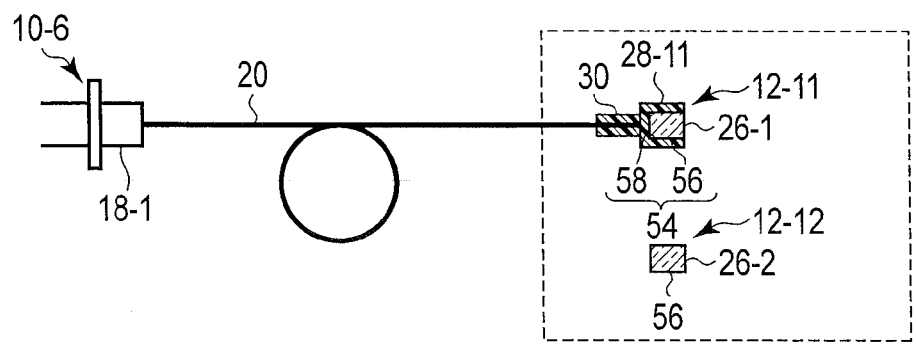
FIG. 12 is a diagram showing a configuration of a light source system according to a modification of a fourth embodiment.

The fourth embodiment illustrates the example in which the connection portion 48 is located between each of the holding members 28-8, 28-9, and 28-10 and the ferrule 30 as shown in FIG. 10. However, the fourth embodiment is not limited to this example. For example, as shown in FIG. 12, a holding member 28-11 and each of the phosphor 26-1 and a phosphor 26-2, which are optical conversion elements, may be configured to be attachable to and removable from each other. That is, a connection portion 54 may be provided between the optical conversion element (26-1 or 26-2) and the holding member 28-11. Only an area of FIG. 12 enclosed by a dotted line is drawn as a cross-sectional view. The connection portion 54 may include a connection surface 56 which is a part of the outer surface of the optical conversion element and which corresponds to one side of the connection portion 54, and a connection surface 58 that is the inner surface of the holding member 28-11. In this case, a light source unit 10-6 includes the semiconductor laser 18-1, the optical fiber 20, the ferrule 30, and the holding member 28-11. An eleventh optical conversion unit 12-11 and a twelfth optical conversion unit 12-12 each include only an optical conversion element (26-1 or 26-2, respectively). This arrangement allows the optical conversion units 12-11 and 12-12 for replacement to be configured using the minimum amount of members. Furthermore, the optical conversion units can be configured to have a very small size. Although not shown in the drawings, the connection surface 56 of each of the optical conversion units 12-11 and 12-12 has its size defined to fit the connection surface 58 of the holding member 28-11 or has a fitting structure that fits and holds the connection surface 58, and is thus prevented from being inadvertently detached from the connection surface 58.

Many modifications of the optical conversion unit other than the above-described examples may be used such as the first to seventh optical conversion units 12-1 to 12-7, described in the first to third embodiments, a wavelength selection filter, and a combination thereof.

[Fifth Embodiment]

Now, a fifth embodiment of the present invention will be described.

The basic configuration of the present embodiment is the same as the basic configuration of the first embodiment. Here, only differences from the first embodiment will be described.

A light source system according to the fifth embodiment is different from the light source systems according to the first to fourth embodiments in the position of a connection portion to and from which a light source unit and an optical conversion unit are attached and removed.

Figure 13:
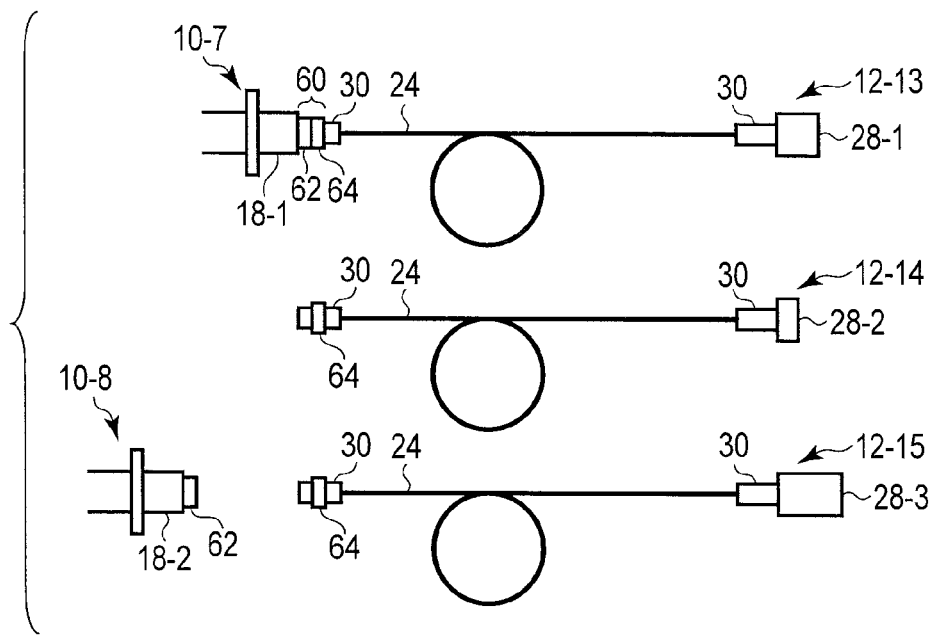
FIG. 13 is diagram showing a configuration of a light source system according to a fifth embodiment of the present invention.

That is, as shown in FIG. 13, the light source system according to the present embodiment is different from the light source system according to the first embodiment in that a connection portion 60 is provided between a semiconductor laser 18-1 or 18-2 and an optical fiber 20 serving as a light guide rather than on an optical fiber 20.

A seventh light source unit 10-7 and an eighth light source unit 10-8 and a thirteenth optical conversion unit 12-13, a fourteenth optical conversion unit 12-14, and a fifteenth optical conversion unit 12-15 are different from the first and second light source units 10-1 and 10-2 and the first, second, and third optical conversion units 12-1, 12-2, and 12-3 illustrated in the first embodiment only in the position and structure of the connection portion. The above-described units of the fifth embodiment have the same optical functions as those of the corresponding above-described units of the first embodiment.

Each of the seventh and eighth light source units 10-7 and 10-8 includes a semiconductor laser 18-1 or 18-2, respectively, the optical fiber 20 and a connector 62 of the connection portion 60 as shown in FIG. 13. Although the connection portion 60 is partly omitted from FIG. 13 for simplification, a connector 62 and a connector 64 have a fitting structure such as a joint which allows the connectors 62 and 64 to be fixed to each other.

The connection portion 60 has a positioning function to place the ferrule 30 in the optimum positional relationship with the semiconductor laser 18-1 or 18-2. A lens or the like may be used to optically connect the ferrule 30 to the semiconductor laser 18-1 or 18-2. In this case, the connection portion 60 has a positioning function to place the lens in the optimum positional relationship with the ferrule 30.

FIG. 13 shows the thirteenth, fourteenth, and fifteenth optical conversion units 12-13, 12-14, and 12-15, which are members belonging to a light source unit group according to the present embodiment.

The structure of an optical output end side of each of the thirteenth, fourteenth, and fifteenth optical conversion units 12-13, 12-14, and 12-15 is similar to the structure in the first embodiment. The thirteenth, fourteenth, and fifteenth optical conversion units 12-13, 12-14, and 12-15 are similar to the first, second, and third optical conversion units 12-1, 12-2, and 12-3 according to the first embodiment except that the connection portion 60 is configured to be suitable for direct connection to the seventh and eighth light source units 10-7 and 10-8.

The connection portion 60 is configured such that the external shape of the ferrule fits the inner diameter of a through-hole in the connector 62 so that the ferrule 30 is positioned to efficiently receive primary light emitted by the semiconductor laser 18-1 or 18-2 of the seventh or eighth light source unit 10-7 or 10-8. When the ferrule 30 and the connector 62 are fitted together and the distal end of the optical fiber 24 is positioned to efficiently receive the primary light, the connectors 62 and 64 are fixed to each other. This adjustably allows the primary light to be more efficiently transmitted through the connection portion 60.

For all possible combinations of the members belonging to the light source unit group and the members belonging to the optical conversion unit group, the basic operation of the light source system according to the fifth embodiment described above is similar to the basic operation described in the first embodiment.

As described above, the light source system according to the fifth embodiment allows the structures of the light source units 10-7 and 10-8 to be simplified without substantially complicating the structures of the optical conversion units. Thus, the light source system according to the fifth embodiment is suitable for a reduction in size and costs.

That is, the configuration according to the present embodiment enables a reduction in the sizes and costs of the light source units 10-7 and 10-8. Furthermore, exclusively the semiconductor laser 18-1 or 18-2, serving as a primary light source, can be replaced. For example, even when the light source apparatus is incorporated into an endoscope or the like, the fifth embodiment enables a replacement operation to be performed more easily than the first to third embodiments. In particular, if lighting is to be provided, for example, under water, a waterproof structure is easily constructed because the connection portion 60 is not located on the distal end side of the optical fiber 24.

Many modifications of the optical conversion unit other than the above-described examples may be used such as the first to seventh optical conversion units 12-1 to 12-7, described in the first to third embodiments, a wavelength selection filter, and a combination thereof.

[Modification of the First to Fifth Embodiments]

Now, a modification of the first to fifth embodiments will be described.

The first to fifth embodiments illustrate only the examples in which the optical fibers 20 and 24 as a light guide. However, the light guide is not limited to the optical fibers, and any of various common light guides may be used. The various available light guides include, for example, a film light guide formed by areas with different refractive indices provided on a film substrate in contact with one another, a semiconductor light guide formed by areas with different refractive indices provided on a semiconductor substrate in contact with one another, and a slab light guide formed of resin or the like.

Figure 14:
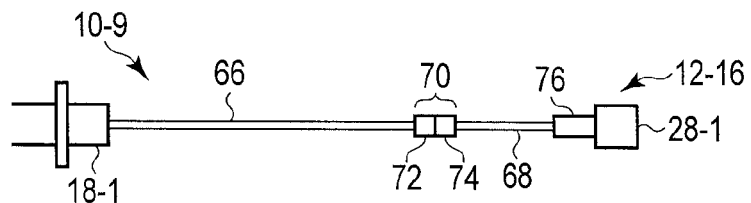
FIG. 14 is a diagram illustrating a modification of the first to fifth embodiments of the present invention.

FIG. 14 is a diagram showing the modification of the first embodiment. FIG. 14 shows an example in which the first light source unit 10-1 and the optical fiber 20 and 24 used for the first optical conversion unit 12-1 are replaced with film light guides 66 and 68. For a ninth light source unit 10-9 and a sixteenth optical conversion unit 12-16, the connection portion 22 and the connectors 14 and 16, which are the components of the connection portion 22, are replaced with a connection portion 70 and connectors 72 and 74 to allow the use of the film light guides 66 and 68. Furthermore, the ferrule 30 is replaced with a light guide end holding member 76.

Figure 15:
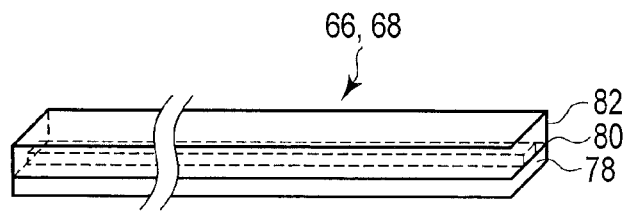
FIG. 15 is a diagram illustrating a configuration of a film light guide.

As shown in FIG. 15, each of the film light guides 66 and 68 includes a light guiding portion 80 formed of a transparent member having a higher refractive index than a film substrate 78 and a transparent cover member 82 disposed on the light guiding portion 80 and having a refractive index approximately equal to the refractive index of the film substrate 78. This configuration hinders light entering the light guiding portion 80 from propagating to the film substrate 78 or the cover member 82 and enables the light to be efficiently guided.

The connection portion 70 may be based on a normal technique such as connectors to and from which film light guides can be attached and removed.

Moreover, if light guides other than the film light guides such as semiconductor light guides or slab light guides are used, the appropriate technique may be selected for the connection portion.

[Sixth Embodiment]

Now, a configuration of a light source system according to a sixth embodiment of the present invention will be described.

Figure 16:
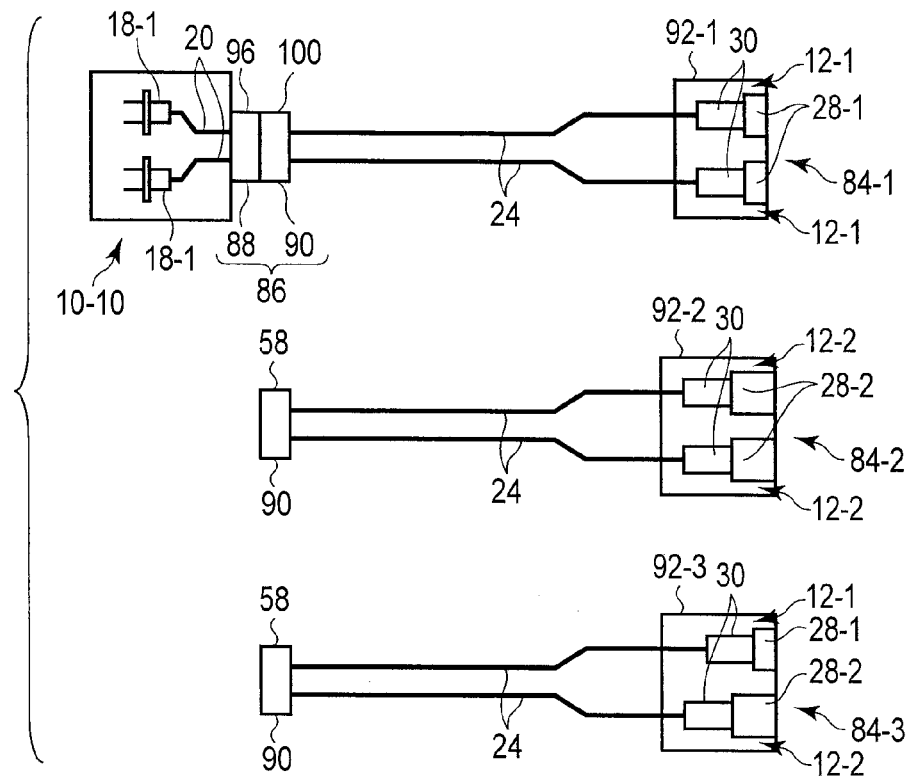
FIG. 16 is diagram showing a configuration of a light source system according to a sixth embodiment of the present invention.

As shown in FIG. 16, the light source system according to the present embodiment includes a tenth light source unit 10-10, a plurality of integrated optical conversion units 84-1, 84-2, and 84-3. A light source apparatus can be provided by combining the tenth light source unit 10-10 with one of the integrated optical conversion units 84-1, 84-2, and 84-3.

The tenth light source unit 10-10 includes two semiconductor lasers 18-1 serving as a primary light source, optical fibers 20 each serving as a first light guide, and a multi-core connector 88 which is included in an integrated connection portion 86 and which is a light source unit side connector serving as a first integrated connection portion. The multi-core connector 88 can be attached to and removed from an opposite multi-core connector 90 serving as a second integrated connection portion on the integrated optical conversion unit 84-1, 84-2, or 84-3 side.

The semiconductor laser 18-1 is a blue semiconductor laser that emits blue light with a wavelength of about 450 nm. The blue semiconductor laser 18-1 and the optical fiber 20 are optically connected together by a lens or the like (not shown in the drawings) and configured such that blue laser light that is primary light emitted by the semiconductor laser 18-1 efficiently enters a core of the optical fiber 20. The blue laser light having entered the optical fiber 20 is guided via the integrated connection portion 86 to the optical conversion unit of the integrated optical conversion unit 84-1, 84-2, or 84-3 connected to the integrated connection portion 86.

Each of the integrated optical conversion units 84-1, 84-2, and 84-3 includes two optical conversion units. Each of the two optical conversion units includes a ferrule 30, two holding members 28-1 or two holding members 28-2 or a holding member 28-1 and a holding member 28-2, and optical conversion elements mounted in the holding members 28-1 and/or 28-2. The two optical conversion units are fixed to one optical conversion unit holding member 92-1, 92-2, or 92-3 to form an integrated optical conversion unit 84-1, 84-2, or 84-3, respectively. Furthermore, a plurality of connection portions provided at a proximal end of a second optical fiber 24 connected to the optical conversion unit and serving as a light guide is aggregated into a second integrated connection portion (multi-core connector 90) as described above.

Figure 17A:
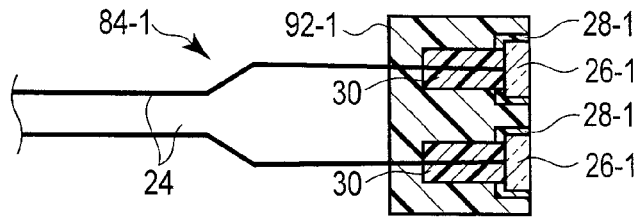
FIG. 17A is a cross-sectional view showing a configuration of a first integrated optical conversion unit.

As shown in FIG. 17A, the first integrated optical conversion unit 84-1 includes two first optical conversion units 12-1 mounted on the optical conversion unit holding member 92-1. Each of the two first optical conversion unit 12-1 includes a holding member 28-1, a phosphor 26-1, and a ferrule 30. The holding member 28-1 is shaped like a bottomed cylinder in which the phosphor 26-1 is interposed, and the phosphor 26-1 is a wavelength conversion member carrying out an optical conversion so as to shift to longer the peak wavelength of the primary light and to broaden the spectrum shape and the radiation angle. Furthermore, an opening through which the primary light passes is formed on a bottom surface of the cylinder of the holding member 28-1. The ferrule 30 and the optical fiber 24 disposed in the ferrule 30 and serving as a second light guide are inserted through the opening.

Figure 17B:
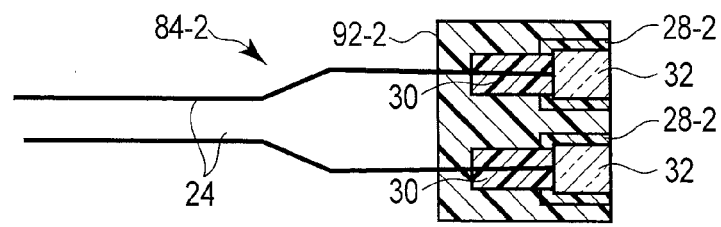
FIG. 17B is a cross-sectional view showing a configuration of a second integrated optical conversion unit.

Furthermore, as shown in FIG. 17B, the second integrated optical conversion unit 84-2 is configured similarly to the first integrated optical conversion unit 84-1. The second integrated optical conversion unit 84-2 is different from the first integrated optical conversion unit 84-1 in the holding member 28-2 with two optical conversion units and an optical conversion element interposed in the holding member 28-2. An optical conversion element in a second optical conversion unit 12-2 of the integrated optical conversion unit 84-2 is a radiation angle conversion element including a diffusion member 32 interposed in the holding member 28-2 and diffusing the primary light.

Figure 17C:
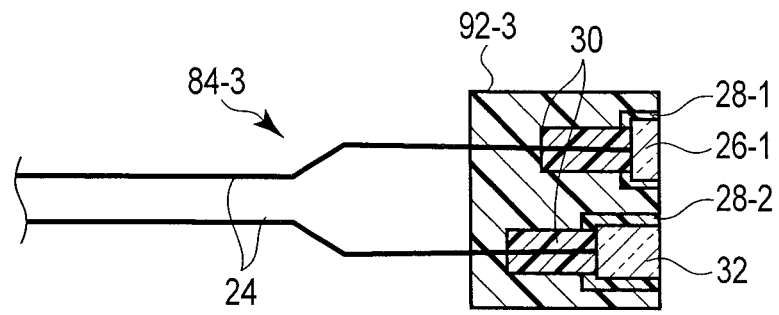
FIG. 17C is a cross-sectional view showing a configuration of a third integrated optical conversion unit.

As shown in FIG. 17C, the third integrated optical conversion unit 84-3 includes the first optical conversion unit 12-1 with the phosphor 26-1 mounted on the first integrated optical conversion unit 84-1 and the second optical conversion unit 12-2 with the diffusion member 32 mounted on the second integrated optical conversion unit 84-2.

Figure 18:
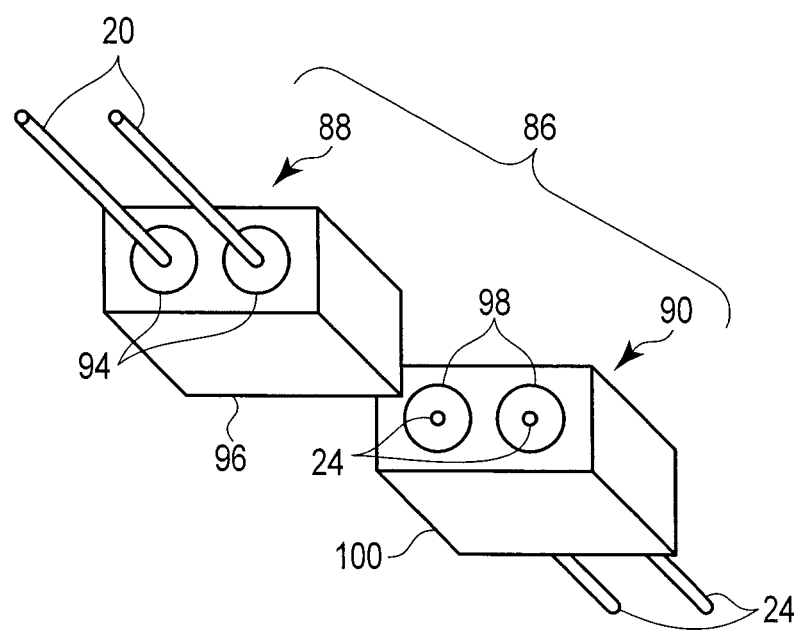
FIG. 18 is a perspective view showing a configuration of an integrated connection portion.

As shown in FIG. 18, the integrated connection portion 86 includes the multi-core connector 88 serving as a first integrated connection portion and the multi-core connector 90 serving as a second integrated connection portion. The multi-core connector 88 mounted on the light source unit 10-10 side includes the optical fibers 20 connected to the respective blue semiconductor lasers 18-1 and first connection portions 94 attached to the distal ends of the respective optical fibers 20. The two first connection portions 94 are attached to a common connection portion holding member 96 to form a multi-core connector 88 serving as a first integrated connection portion.

Similarly, the integrated optical conversion unit side multi-core connector 90 includes the optical fibers 24 and second connection portions 98 attached to the proximal ends of the respective optical fibers 24. The two second connection portions 98 are attached to a common connection portion holding member 100 to form a multi-core connector 90 serving as a second integrated connection portion.

The multi-core connectors 88 and 90 are configured so as to fix, by a fitting portion (not shown in the drawings), the optical fibers 20 and 24 at positions where the optical fibers are efficiently optically connected together. The fitting portion may be based on a common optical connector technique. Furthermore, for example, a multi-core ferrule may be used which is like a plurality of integrated connection portions.

Now, the operation of the light source system according to the present embodiment will be described.

As described above, the light source system allows the plurality of integrated optical conversion units 84-1, 84-2, or 84-3 to be replaced for the tenth light source unit 10-10.

First, the operation of a combination of the tenth light source unit 10-10 with the first integrated optical conversion unit 84-1 will be described.

The tenth light source unit 10-10 and the first integrated optical conversion unit 84-1 are connected together by the integrated connection portion 86. The semiconductor lasers 18-1 mounted on the tenth light source unit 10-10 are allowed to emit light. Then, blue laser light emitted by the semiconductor lasers 18-1 is delivered to the phosphor 26-1 of the first optical conversion units 12-1 through the integrated connection portion 86 and the second optical fibers 24. The phosphors 26-1 have its thickness and fluorescent material content adjusted so as to absorb a portion of the blue laser light to convert the portion into yellow light while transmitting the remaining portion of the blue laser light so that the yellow light resulting from the conversion and the transmitted blue light form white light. Therefore, when the blue laser light emitted by the semiconductor lasers 18-1 is delivered to the phosphors 26-1, white light is emitted as illumination light.

According to the present embodiment, the two semiconductor lasers 18-1 of the light source unit 10-10 are configured to have the same characteristics, and the two first optical conversion units 12-1 of the first integrated optical conversion unit 84-1 are configured to have the same characteristics. Thus, regardless of whether the two semiconductor lasers 18-1 are turned on or any one of the two semiconductor lasers 18-1 is turned on, the properties of emitted white light are the same. However, the irradiation pattern or intensity distribution of delivered white light can be adjusted based on the manner of lighting the two semiconductor lasers 18-1. Furthermore, the system may be designed such that an irradiation pattern or intensity distribution suitable for an illumination target can be obtained by adjusting a mounting portion on the optical conversion unit holding member 92-1 which allows the first optical conversion units 12-1 to be mounted thereon. Additionally, operation of each of the semiconductor lasers up to a brightness limit allows the resultant brightness to be doubled compared to operation of only one of the semiconductor lasers up to the brightness limit.

Now, the operation of a light source apparatus with a combination of the tenth light source unit 10-10 with the second integrated optical conversion unit 84-2 will be described. The basic operation of this light source apparatus is similar to the basic operation of the above-described light source apparatus using the first integrated optical conversion unit 84-1.

The optical conversion elements of the second optical conversion units 12-2 mounted on the second integrated optical conversion unit 84-2 are the diffusion members 32. The diffusion member 32 has the property of broadening the radiation angle of blue laser light emitted by the semiconductor laser 18-1. Furthermore, upon passing through the diffusion member 32, the laser light has its coherence length reduced and is hindered from forming speckles or the like on the illumination target. Thus, with this combination, turning on of the semiconductor lasers 18-1 enables emission of blue laser light, which has a divergence angle suitable for illumination of the target and which is unlikely to form speckles and the like.

Now, the operation of a light source apparatus with a combination of the tenth light source unit 10-10 with the third integrated optical conversion unit 84-3 will be described. The basic operation of this light source apparatus is similar to the basic operations of the above-described light source apparatuses using the first and second integrated optical conversion units 84-1 and 84-2.

The optical conversion elements of the first and second optical conversion units 12-1 and 12-2 mounted on the third integrated optical conversion unit 84-3 are one phosphor 26-1 and one diffusion member 32. When the semiconductor laser 18-1 optically connected to the phosphor 26-1 is turned on, the first optical conversion unit 12-1 emits white light. Furthermore, when the semiconductor laser 18-1 optically connected to the diffusion member 32 is turned on, the second optical conversion units 12-2 emits diffused blue illumination light.

As described above, the light source system according to the sixth embodiment allows illumination light suitable for illuminating various intended illumination targets to be obtained by replacing only the integrated optical conversion unit 84-1, 84-2, or 84-3 for the tenth light source unit 10-10. Furthermore, according to the light source system according to the sixth embodiment, a plurality of optical conversion units is integrated into the integrated optical conversion unit 84-1, 84-2, or 84-3 to enable design of an irradiation pattern and provision of a brighter light source apparatus. Additionally, the use of the third integrated optical conversion unit 84-3 with two different optical conversion units enables the illumination light to be instantaneously switched by turning the semiconductor lasers on and off. In this case, a plurality of connection portions is integrated into the integrated connection portion 86 and is thus simultaneously attachable and removable.

That is, the light source system according to the sixth embodiment allows the plurality of integrated optical conversion units 84-1, 84-2, and 84-3 to be replaced for one light source unit 10-10, thus enabling a small number of members to generate more types of illumination light.

Furthermore, when a plurality of optical conversion units is integrated into the integrated optical conversion unit 84-1, 84-2, or 84-3, the irradiation pattern can be designed according to the illumination target, a brighter light source apparatus can be provided, and a light source apparatus can be provided which allows different illumination light colors to be instantaneously switched by turning the light sources on and off. In this case, a plurality of connection portions is integrated into the integrated connection portion 86 and is thus easily simultaneously attachable and removable without erroneous connection.

In the above-described sixth embodiment, the system includes the one type of light source unit and the three types of integrated optical conversion units for simplification. However, for practical use, more light source units and more integrated optical conversion units may be appropriately prepared according to the demanded functions of the illumination light. The primary light source mounted on the light source unit is not limited to the semiconductor laser 18-1 but may be any of various light sources such as various laser light sources, a LED, and a lamp. More desirably, the light source is efficiently connectible to the optical fiber.

Furthermore, the optical conversion element mounted on the optical conversion unit is also not limited to the above-described phosphor or diffusion member but may be any of various optical conversion elements. Examples of the usable optical conversion element include not only various powdery phosphors, ceramic phosphors, and single crystal phosphors, but also a quantum dot, a semiconductor light emitting element, and an organic light emitting element. Additionally, when a filter that cuts a portion of the wavelength of fluorescence is disposed on an output surface of the phosphor, exclusively the fluorescence in the desired wavelength region can be extracted. Alternatively, mounting a filter that cuts the primary light enables only the fluorescence to be extracted. Furthermore, the diffusion member may be of a type including a transparent member the surface of which is processed to include recesses and protrusions. Moreover, when various optical conversion units are used such as a lens group configured to adjust the radiation angle, a diffraction grating, a polarizing element, and a photonic crystal, the radiation angle or intensity distribution of emitted secondary light can be optimized or made directional. In addition, the use of various wavelength filters enables only the light in the desired wavelength range to be extracted or cut.

[Seventh Embodiment]

Now, a seventh embodiment of the present invention will be described.

The basic configuration of the seventh embodiment is the same as the basic configuration of the sixth embodiment. Thus, only differences from the sixth embodiment will be described.

The light source system according to the present embodiment is configured as shown in FIG. 19 and basically configured similarly to the light source system in the sixth embodiment shown in FIG. 16. The seventh embodiment is different from the sixth embodiment in the number of primary light sources in a light source unit, the number of optical conversion units in an integrated optical conversion unit, and the number of connection portions in an integrated connection portion.

That is, the present embodiment illustrates an example of an integrated optical conversion unit group with integrated optical conversion units. In the integrated optical conversion unit group, when effective light source unit side connection portions are defined as those of the connection portions of a first integrated connection portion provided on a light source unit which are optically connected to a primary light source and effective optical conversion unit side connection portions are defined as those of the connection portions of a second integrated connection portion provided on an integrated optical conversion unit which are optically connected to optical conversion units, the effective light source side connection portions are different, in number, from the effective optical conversion unit side connection portions. The present embodiment describes an example of an integrated optical conversion unit group with integrated optical conversion units in which the effective optical conversion unit connection portions are fewer than the effective light source side connection portions.

As shown in FIG. 19, the light source unit according to the present embodiment is an eleventh light source unit 10-11 with two semiconductor lasers 18-1 and two semiconductor lasers 18-2 in which the semiconductor lasers 18-1 and 18-2 are of different types. The eleventh light source unit 10-11 includes the semiconductor lasers 18-1, which emit 450-nm blue laser light as is the case with the sixth embodiment, and the semiconductor lasers 18-2, which are different from the semiconductor lasers 18-1 and emit 405-nm blue-violet laser light. A first optical fiber 20 is connected to each of the total of four semiconductor lasers 18-1 and 18-2 and to a multi-core connector 102 serving as a first integrated connection portion. That is, the multi-core connector 102 includes four connection portions. In other words, a connection portion holding member 96 provided on the light source unit 10-11 includes four connection portion mounting positions to all of which connection portions are mounted.

The remaining part of the configuration is similar to the corresponding part of the sixth embodiment.

On the other hand, the integrated optical conversion unit according to the present embodiment includes three integrated optical conversion units 84-4, 84-5, and 84-6 as members. The fourth integrated optical conversion unit 84-4 includes a total of four optical conversion units including two holding members 28-1 each with a phosphor 26-1 interposed therein as is the case with the sixth embodiment and two holding member 28-16 each with a phosphor 26-5 mounted thereon to optically convert 405-nm blue-violet light into red light. The four optical conversion unit 12-1 and 12-16 are fixed to one optical conversion unit holding member 92-4. Furthermore, the fourth integrated optical conversion unit 84-4 includes a multi-core connector 104 serving as a second integrated connection portion with four connection portions. Four optical fibers 24 extending from the respective connection portions are connected to respective holding members 28-1 and 28-2.

Furthermore, the fifth integrated optical conversion unit 84-5 includes only the two first optical conversion units 12-1, including the phosphors 26-1 and included in the four optical conversion units mounted on the fourth integrated optical conversion unit 84-4. The two first optical conversion units 12-1 are fixed to one optical conversion unit holding member 92-5. Additionally, the fifth integrated optical conversion unit 84-5 includes the multi-core connector 104 serving as a second integrated connection portion with four connection portions. Second optical fibers 24 are connected to ports optically connected to two of the four connection portions of the multi-core connector that are connected to the semiconductor lasers 18-1 of the light source unit 10-11. Each of the second optical fibers 24 extends to the corresponding optical conversion unit with the phosphor 26-1 mounted thereon. In addition, each of the two remaining ports includes a shutter 106 serving as a light blocking member that prevents laser light from leaking to the exterior. That is, the number of effective connection portions is two. Here, the number of effective connection portions refers to the number of connection portions each with the distal end thereof connected to the optical conversion unit and does not involve apparent connection portions with no actual connection. In other words, the connection portion holding member 100 includes four connection portion attachable positions so that the connection portions are attached at two of these positions, whereas the shutters 106 are attached at the remaining two positions.

Furthermore, the sixth integrated optical conversion unit 84-6 includes a total of two optical conversion units included in the four optical conversion units mounted on the fourth integrated optical conversion unit 84-4, the two optical conversion units including one first optical conversion unit 12-1 with the phosphor 26-1 and one sixteenth optical conversion unit 12-16 with the phosphor 26-5. The two optical conversion units 12-1 and 12-6 are fixed to one optical conversion unit holding member 92-6. Additionally, the sixth integrated optical conversion unit 84-6 includes the multi-core connector 104 serving as a second integrated connection portion with four connection portions. Second optical fibers 24 are connected to a total of two connection ports, that is, one of those two connection portions of the four connection portions of the multi-core connector 104 which are connected to the semiconductor lasers 18-1 of the light source unit 10-11 and to one of those two connection portions of the four connection portions of the multi-core connector 104 which are connected to the semiconductor lasers 18-2 of the light source unit 10-11. Each of the second optical fibers 24 extends to the corresponding optical conversion unit with the phosphor 26-1 or 26-5. In addition, each of the two remaining ports includes the shutter 106 serving as a light blocking member that prevents laser light from leaking to the exterior. That is, the number of effective connection portions is two. In other words, the connection portion holding member 100 includes four connection portion attachable positions so that the connection portions are attached at two of these positions, whereas the shutters 106 are attached at the two remaining positions.

The appropriate design according to the purpose can be applied to the arrangement of the individual optical conversion units on the optical conversion unit holding members 92-4, 92-5, and 92-6 in the integrated optical conversion units 84-4, 84-5, and 84-6.

Figure 20B:
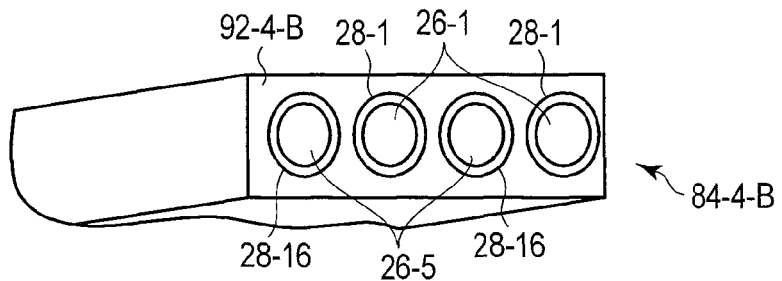
FIG. 20B is a diagram showing another example of configuration of the fourth integrated optical conversion unit.

FIG. 20A shows an example of a configuration using, for example, a cylindrical optical conversion unit holding member 92-4-A, and FIG. 20B shows an example of a configuration using, for example, a plate-like optical conversion unit holding member 92-4-B. The example of the fourth integrated optical conversion unit 84-4-A shown in FIG. 20A is suitable for illuminating the interior of a thin hole or the like. The example of the fourth integrated optical conversion unit 84-4-B shown in FIG. 20B is suitable for illuminating the interior of a thin crack-like gap. Thus, even the integrated optical conversion units 84-4, 84-5, 84-6 with the same optical conversion unit mounted thereon allows the size and shape of the distal end unit to be made suitable for the purpose by changing an attachment position on the optical conversion unit holding member 92-4, 92-5, or 92-6. Furthermore, the shape of the irradiation pattern delivered to the illumination target can be made suitable for the purpose.

Now, the operation of the light source system according to the seventh embodiment will be described. The operation is basically the same as the operation of the light source system according to the sixth embodiment. Here, only differences from the sixth embodiment will be described.

First, the operation of a light source apparatus with a combination of the eleventh light source unit 10-11 with the fourth integrated optical conversion unit 84-4 will be described.

Figure 21:
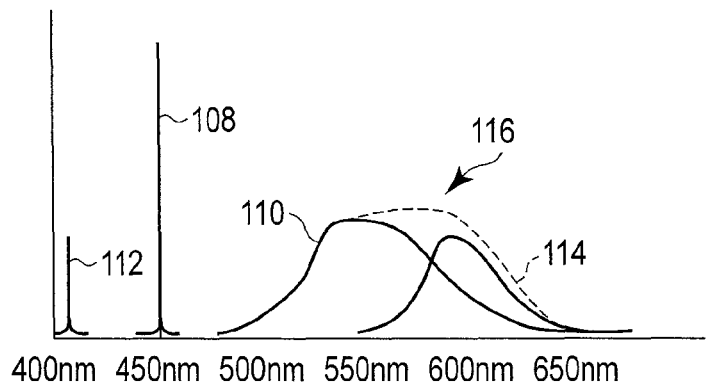
FIG. 21 is a diagram illustrating the operation of a combination of an eleventh light source unit with the fourth integrated optical conversion unit.

Blue laser light emitted by the semiconductor lasers 18-1 is guided to the phosphors 26-1 via the optical fibers 20 and 24. The phosphors 26-1 convert a portion of the blue laser light into yellow fluorescence while transmitting the remaining portion, to emit white light. The spectrum of the emitted white light is shown in FIG. 21. In FIG. 21, a spectrum resulting from turning on of the blue semiconductor lasers 18-1 contains blue laser light 108 and yellow fluorescence 110. The corresponding illumination light appears to be white light, but light of a red component which is 600 nm or more in wavelength is weak.

Blue-violet laser light emitted by the semiconductor lasers 18-2 is guided to the phosphors 26-5 via the optical fibers 20 and 24. The phosphors 26-5 convert a portion of the blue-violet laser light into red fluorescence. In FIG. 21, a spectrum resulting from turning on of the blue-violet semiconductor lasers 18-2 contains blue-violet laser light 112 and red fluorescence 114. The present embodiment illustrates the example in which the phosphors 26-5 absorb a portion of the blue-violet laser light 112 to convert the portion into red fluorescence 114 while transmitting the remaining portion. However, the phosphors 26-5 may be configured to convert all of the blue-violet laser light 112 into the red fluorescence 114.

That is, when both the semiconductor lasers 18-1 and 18-2 are turned on, the spectrum of illumination light emitted by the fourth integrated optical conversion unit 84-4 contains the blue-violet laser light 112, the blue laser light 108, and fluorescence 16 with the yellow fluorescence 110 and the red fluorescence 114 overlapping each other as shown in FIG. 21.

Now, the operation of a combination of the light source unit 10-11 with the fifth integrated optical conversion unit 84-5 will be described.

An operation resulting from turning on of the semiconductor lasers 18-1 is similar to the operation associated with a combination of the light source unit 10-10 with the first integrated optical conversion unit 84-1 according to the sixth embodiment.

On the other hand, when the semiconductor lasers 18-2 is turned on, blue-violet laser light is fed from a connection portion of the multi-core connector 102 with the light source unit 10-11 which portion is connected to the semiconductor lasers 18-2 to a connection portion of the multi-core connector 104 of the fifth integrated optical conversion unit 84-5 which portion has no connection. However, the connection portion with no connection includes the shutters 106 serving as a light blocking member that prevents laser light from leaking to the exterior, thus blocking the laser light by the shutters 106 to prevent the laser light from leaking to the exterior.

Now, the operation of a combination of the light source unit 10-11 with the sixth integrated optical conversion unit 84-6 will be described.

An operation resulting from turning on of the semiconductor lasers 18-1 and 18-2 on the light source unit 10-11 optically connected to the phosphors 26-1 and 26-5 via the multi-core connectors 102 and 104 is basically similar to the operation associated with the connection between the light source unit 10-11 and the fourth integrated optical conversion unit 84-4 as described above. In the above-described example, two semiconductor lasers 18-1 are combined with two optical conversion units with the respective phosphors 26-1, and two semiconductor lasers 18-2 are combined with two optical conversion units with the respective phosphors 26-5. When the light source unit 10-11 is combined with the sixth integrated optical conversion unit 84-6, one semiconductor laser 18-1 is combined with one optical conversion unit with the phosphor 26-1, and one semiconductor laser 18-2 is combined with one optical conversion unit with the phosphor 26-5, but the operation is similar to the operation in the above-described example.

Furthermore, the operation of a connection portion of the multi-core connector 102 of the light source unit 10-11 which portion has no connection is similar to the above-described operation associated with the fifth integrated optical conversion unit 84-5. Laser light delivered to the shutters 106 is absorbed by the shutters 106 and prevented from leaking to the exterior.

As described above, in the light source system according to the seventh embodiment, different primary light sources are mounted on one light source unit 10-11, different numbers of optical conversion units with different functions are mounted on the integrated optical conversion units 84-4, 84-5, and 84-6, and various types of needed illumination light can be provided by appropriately combining the light source unit with any of the integrated optical conversion units.

That is, the present embodiment allows any of the integrated optical conversion units 84-4, 84-5, and 84-6 to be selected according to the characteristics of needed illumination light. That is, in the configuration according to the sixth embodiment, the light of the red component is slightly weaker than the other colors, and the weak light of the red component may pose a problem depending on the illumination target. For example, when a red object is to be illuminated, illumination light with few red components makes the object appear dark. The configuration according to the present embodiment may combine the light source unit 10-11 with the fourth integrated optical conversion unit 84-4 for applications needing bright red components and may use the fifth integrated optical conversion unit 84-5 for applications not emphasizing red components. The fifth integrated optical conversion unit 84-5 includes only a small number of, that is, two optical conversion units mounted thereon and can thus be small and inexpensive. Furthermore, if brightness is unwanted but red components are needed, the needed light can be obtained by using the sixth integrated optical conversion unit 84-6. The sixth integrated optical conversion unit 84-6 is also small and inexpensive.

Thus, an illumination apparatus corresponding to an application can be provided using the common light source unit 10-11.

The present embodiment illustrates the example in which the light source unit includes two primary light sources mounted thereon and emitting one type of light and two other primary light sources mounted thereon and emitting a different type of light. However, the present embodiment is not limited to this example. Three or more types of primary light sources may be mounted on the light source unit depending on the application. Such a configuration can provide a brighter light source apparatus and implement illumination light in more colors and with different spectra.

Furthermore, the present embodiment illustrates the example in which the connection portion uses four-core connectors. However, the present embodiment is not limited to this example. At least two cores enable different types of illumination light to be implemented according to the connection. Additionally, at least five cores enable more different types of illumination light to be implemented.

Moreover, the present embodiment illustrates the example in which the color rendering index for red is improved by adding red fluorescence to yellow fluorescence. The present embodiment is not limited to this example. For example, the intensity of a blue component can be improved by using a phosphor that converts 405-nm blue-violet laser light into blue. This allows a blue object to be brightly illuminated.

According to such a light source system, for a user who does not particularly need brightness and who is to utilize white light and white light with a red component added thereto, a small, inexpensive illumination apparatus can be implemented by providing a light source unit with a reduced number of primary light sources.

Figure 22:
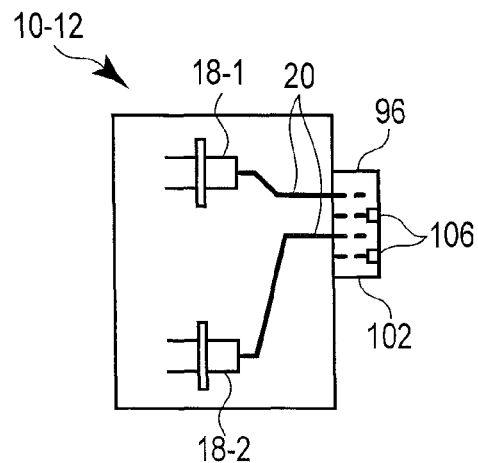
FIG. 22 is a diagram showing a twelfth light source unit.

A twelfth light source unit 10-12 shown in FIG. 22 includes one semiconductor laser 18-1 emitting blue light and one semiconductor laser 18-2 emitting blue-violet light. The multi-core connector 102 serving as a first integrated connection portion is connectible to any of the integrated optical conversion units 84-4, 84-5, and 84-6 illustrated in the seventh embodiment. In a combination of the twelfth light source unit 10-12 with the sixth integrated optical conversion unit 84-6, white light can be obtained by turning only the semiconductor laser 18-1 on, and the red component can be added to the white color by further turning the semiconductor laser 18-2 on. In this case, the number of effective connection portions is two. Furthermore, two ineffective connection portions include the shutter 106 as a cover. In other words, the connection portion holding portion 96 includes four connection portion mountable positions so that the connection portions are attached at two of these positions, whereas the shutters 106 are attached at the remaining two positions.

Furthermore, if brighter illumination light is needed for the future, the light source can be stepped up by purchasing the eleventh light source unit 10-11 and the fourth integrated optical conversion unit 84-4. In this case, the already owned sixth integrated optical conversion unit 84-6 can be continuously used.

Moreover, a user who owns the eleventh light source unit 10-11 and a plurality of integrated optical conversion units can utilize such a small light source unit 10-12 as a reserve or handy light source unit.

That is, the eleventh light source unit 10-11 and the twelfth light source unit 10-12 form a light source unit group. The user can obtain a light source unit meeting the user's purpose from the light source unit group or add the light source unit group to the user's owned light source system.

Now, a modification of the light source unit according to the seventh embodiment will be described.

The present modification illustrates a configuration of a light source unit configured differently from the above-described light source units and which can be combined, for use, with any of the integrated optical conversion units 84-4, 84-5, and 84-6 described in the seventh embodiment.

The eleventh light source unit 10-11 described in the seventh embodiment uses four semiconductor lasers, that is, the two semiconductor lasers 18-1 emitting blue light and the two semiconductor lasers 18-2 emitting blue-violet light. As shown in FIG. 23, a thirteenth light source unit 10-13 according to the present modification includes one semiconductor laser 18-1 and one semiconductor laser 18-2. The thirteenth light source unit 10-13 is combined with a 1×2 optical coupler 118 with one input end and two output ends to allow blue light and/or blue-violet light to be emitted through a connection port of the multi-core connector 102 serving as a first integrated connection portion. That is, a part of the light guide corresponding to the optical fiber 20 is replaced with the optical coupler 118. The optical coupler is based on a common optical fiber technique and produced by a method for optical coupling of a core portion of the optical fiber.

In such a configuration, laser light emitted by the semiconductor lasers 18-1 and 18-2 enters input ends of the optical couplers 118, where the light is split into two light beams in the respective optical paths. The light beams are then emitted through two of the four connection portions of the multi-core connector 102. The subsequent operation is similar to the corresponding operation according to the seventh embodiment.

Such a configuration allows a reduced number of semiconductor lasers to emit illumination light through an increased number of optical conversion units in the integrated optical conversion unit 84-4, 84-5, or 84-6.

This enables an increase in the number of light emission points in the integrated optical conversion unit to be increased above the number of semiconductor lasers. As a result, for example, when a close illumination target is to be illuminated, an illumination light output portion may be arranged so as to hinder shading. Furthermore, a reduced number of semiconductor lasers enable a compact light source unit to be inexpensively provided.

The present modification illustrates the example using the 1×2 optical coupler 118. However, the present modification is not limited to this example. For example, the use of a 1×3 or larger multi-branch type allows the use of an increased number of optical conversion units. Thus, the illumination pattern can be more freely designed, for example, so as to hinder shading.

Alternatively, an optical coupler with a plurality of input ends may use, and a monitor for optical feedback is connected to one of the input ends. This allows monitoring of the status of laser light fed back from the optical conversion unit and light subjected to optical conversion.

For example, FIG. 24 shows an example in which a fourteenth light source unit 10-14 uses a 2×2 optical coupler 120 with two input ends and two output ends. A photodetector 122 is disposed on one of the two input ends of each of the two optical couplers 120 that is not connected to the semiconductor laser 18-1 or 18-2. Thus, the photodetector 122 can detect optical feedback, that is, laser light emitted by the semiconductor laser 10 and fed back to the emission side after being delivered to the optical conversion unit optically connected to the semiconductor laser 10, as well as light subjected to optical conversion.

Moreover, the modification of the seventh embodiment illustrates the example in which the optical coupler is provided on the light source unit 10-13 or 10-14 side. However, the optical coupler may be used on the integrated optical conversion unit side. This enables an increase in the number of optical conversion units in the integrated optical conversion unit without increasing the number of connection portions.

Exemplary types of optical conversion units mounted on the integrated optical conversion unit include not only the exemplary optical conversion units illustrated in the sixth and seventh embodiments but also various modifications thereof. For example, the optical conversion unit may be modified to offer enhanced thermal resistance to enable stronger primary light to be converted, or a wavelength conversion filter, a plurality of phosphors mixed or stacked, or a combination of a plurality of such optical conversion units may be used.

[Modification of the Sixth and Seventh Embodiments]

Now, a modification of the sixth and seventh embodiments will be described.

Like the first to fifth embodiments, the sixth and seventh embodiments allow various light guides to be utilized. In this case, a plurality of light guides may be formed on one substrate.

Similarly, the optical couplers 118 and 120 serving as light guides are not limited to optically coupled optical fibers, and optical couplers based on various common light guides may be used. The various light guides may include the above-described film light guide, a semiconductor substrate light guide, and a slab light guide formed of resin.

Here, as the film light guide, a film light guide 68 as shown in FIG. 15 may be used.

FIG. 25 is a perspective view of an example of the optical coupler 118 based on a film light guide technique as viewed from an upper surface of the optical coupler 118. Primary light entering an input end 124 is split into two light beams in the respective paths. The light beams are then emitted through respective output ends 128.

The integrated connection portion 86 may be based on a normal technique such as connectors to and from which film light guides can be attached and removed.

Moreover, if light guides other than the film light guides such as semiconductor light guides or slab light guides are used, the appropriate technique may be selected for the connection portion.

The present invention has been described based on the embodiments. However, of course, the present invention is not limited to the above-described embodiments, and various modifications and applications may be made to the embodiments without departing from the scope of the present invention.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A light source unit for use with an endoscope, the light source unit comprising:
    a primary light source configured to emit primary light; and
    a first connector provided on an optical path of the primary light and to which each of a plurality of optical conversion units are attachable and removable, wherein
    each of the plurality of the optical conversion units include
        an optical conversion element having an optical conversion function to convert optical properties of the primary light to generate secondary light and each of the plurality of the optical conversion units further having a second connector configured to detachably engage the first connector to transmit the primary light to the optical conversion element; and
    an optical conversion unit is selected from the plurality of optical conversion units based on the optical conversion function desired for the secondary light.

2. A light source system comprising:
    the light source unit according to claim 1; and
    an optical conversion unit selected from the plurality of optical conversion units having the second connector detachably engaged with the first connector.

3. The light source system according to claim 2, wherein the plurality of optical conversion units each providing a different optical conversion function to optically convert the primary light into secondary light with a different optical property.

4. The light source system according to claim 3, wherein the optical conversion function includes one or more of a peak wavelength, a spectral shape, and a radiation angle.

5. The light source system according to claim 3, wherein the plurality of optical conversion units include an optical conversion unit with functions to convert a radiation angle and to avoid converting a peak wavelength and a spectral shape, the radiation angle, the peak wavelength, and the spectral shape being included in the optical properties of the primary light.

6. The light source system according to claim 5, wherein the optical conversion element of the optical conversion unit is a radiation angle conversion element, and the radiation angle conversion element is one of a diffusion member configured to broaden a radiation angle of the primary light and a lens configured to one of focus and scatter the primary light.

7. The light source system according to claim 2, wherein the plurality of optical conversion units having different input limitations on optically convertible optical properties including a wavelength, a spectrum, and a light intensity of the primary light.

8. The light source system according to claim 7, wherein
at least one optical conversion element of the plurality of optical conversion units is a wavelength conversion member configured to convert the primary light into light with a peak wavelength and a spectrum different from a peak wavelength and a spectrum of the primary light, and
at least some of the plurality of optical conversion units comprising wavelength conversion members with different absorption rates for the wavelength of the primary light.

9. The light source system according to claim 7, wherein at least some of the plurality of optical conversion units having different thermal resistance properties for heat generated in a corresponding optical conversion element during a process from incidence of the primary light to emission of the secondary light.

10. The light source system according to claim 7, wherein at least some of the plurality of optical conversion units exhibiting different thermal radiation properties in radiating heat to an exterior of an optical conversion unit exhibiting the different thermal radiation properties, the heat being generated in the optical conversion unit exhibiting the different thermal radiation properties during a process from incidence of the primary light to emission of the secondary light.

11. The light source system according to claim 7, wherein at least some of the plurality of optical conversion units having different secondary light output area sizes and/or shapes.

12. The light source system according to claim 2, wherein
the light source unit comprises a plurality of light source units each emitting a different primary light, and
each of the plurality of light source units include the first connector.

13. The light source system according to claim 12, wherein at least some of the plurality of light source units emitting primary light differing in at least one of a peak wavelength, a spectrum shape, and a maximum optical output.

14. The light source system according to claim 2, further comprising:
light guides configured to optically connect the light source unit to a selected one of the plurality of optical conversion units,
wherein
the light guides comprise a first light guide optically connected between the primary light source and the first connector and a second light guide optically connected between the second connector and a corresponding optical conversion unit of the selected one of the plurality of optical conversion units.

15. The light source system according to claim 14, wherein the light guides are one of an optical fiber and a film light guide.

16. The light source system according to claim 2, wherein
each of the plurality of optical conversion units further includes a light guide optically connected to a corresponding optical conversion element, and
the first and second connectors are provided between the primary light source and the light guide.

17. The light source unit according to claim 1, wherein
the light source unit further comprises a light guide configured to optically connect the primary light source to the first connector.

18. A plurality of optical conversion units, each of which is for use with an endoscope, each of the optical conversion units comprising:
an optical conversion element configured to convert optical properties of primary light to generate secondary light, the optical conversion element being selected from a plurality of optical conversion elements corresponding to the plurality of optical conversion units, wherein at least some of the plurality of optical conversion elements having different optical conversion functions; and
a first connector provided on an optical path of the primary light for each of the plurality of optical conversion elements, each of the first connectors being attachable to and removable from a second connector, the first and second connectors optically connecting a light source unit including a primary light source configured to emit the primary light to each of the plurality of optical conversion elements.

19. A light source apparatus for use with an endoscope, the light source apparatus comprising:
a light source unit with a primary light source configured to emit primary light;
an optical conversion unit holder for holding a plurality of optical conversion units, each having an optical conversion element configured to convert optical properties of the primary light to generate secondary light, the optical conversion unit holder being selected from a plurality of optical conversion unit holders;
a plurality of light guides configured to optically connect the primary light source to the plurality of optical conversion units by respective light guides; and
a connector for optically connecting the primary light source to each of the plurality of optical conversion unit holders.

20. The light source apparatus according to claim 19, wherein
the connector comprises a first connector having first connection portions attached to a light source unit side and a second connector having second connector portions attached to an optical conversion unit side,
the first connector portions are integrated together to form a first integrated connection portion,
the second connector portions are attached to a connection portion holding member to form a second integrated connection portion, and
the first connector and the second connector form a removable integrated connection portion.

21. The light source apparatus according to claim 20, wherein
a number of effective first connection portions in the first connector is a number of first connection portions optically connected to the primary light source, and a number of effective second connection portions in the second connector is a number of -second connection portions attached to the connection portion holding member of the second connector, and
the number of effective first connection portions in the first connector is greater than or equal to the number of second effective connection portions in the second connector.

22. The light source apparatus according to claim 21, wherein the connection portion holding member includes connection portion attachment positions to which the second connection portions are attachable, and a light blocking member configured to prevent the primary light from leaking to an exterior is provided at each of connection portion attachment positions to which the second connector portions are not attached.

23. The light source apparatus according to claim 20, wherein a number of primary light sources in the light source unit is less than or equal to the number of the first connection portions.

24. The light source apparatus according to claim 20, wherein
each of the plurality of optical conversion units comprises an optical conversion function for at least one of a peak wavelength, a spectral shape, and a radiation angle included in the optical properties of the primary light, and
the optical conversion unit holder includes a plurality of optical conversion units with the wavelength conversion functions which are different from one another.

25. A light source system comprising:
the light source apparatus according to claim 20, and
wherein the optical conversion unit holder forms an integrated optical conversion unit group together with a plurality of integrated optical conversion units different from the optical conversion unit holder, and
the integrated optical conversion units which are members of the integrated optical conversion unit group are all attachable to and removable from the light source unit at the removable integrated connection portion.

26. The light source system according to claim 25, wherein the integrated optical conversion unit group includes a plurality of integrated optical conversion units each with the plurality of optical conversion units attached on the optical conversion unit holder at different positions.

27. The light source system according to claim 25, wherein the integrated optical conversion unit group comprises an integrated optical conversion unit including optical conversion units, each of the optical conversion units having a different optical conversion function for at least one of a peak wavelength, a spectral shape, and a radiation angle included in the optical properties of the primary light.

28. The light source system according to claim 25, wherein the integrated optical conversion unit group includes at least one integrated optical conversion unit with optical conversion units and at least one integrated optical conversion unit with optical conversion units which are different from, in number, the optical conversion units of the integrated optical conversion unit.

29. A light source system using the light source apparatus according to claim 20, wherein
the light source unit forms a light source unit group together with a plurality of light source units different from the light source unit, and
members of the light source unit group are all attachable to and removable from members of the plurality of optical conversion units at the removable integrated connection portion.

30. The light source system according to claim 29, wherein the light source unit group comprises members which are able to radiate primary light among which at least one of a peak wavelength, a spectral shape, and a maximum output varies, the peak wavelength, the spectral shape, and the maximum output being included in optical properties of the primary light emitted by the light source unit.

31. The light source system according to claim 29, wherein the light source unit group comprises members among which a number of primary light sources in the light source unit varies.

32. The light source system according to claim 29, wherein the light source unit group comprises members among which a number of the first connection portions in the first integrated connection portion varies.

33. The light source apparatus according to claim 20, wherein at least one of the plurality of light guides is one of an optical fiber and a film light guide.

* * * * *